United States Patent
Yang et al.

(10) Patent No.: US 10,560,272 B2
(45) Date of Patent: Feb. 11, 2020

(54) BIO-INFORMATION DATA PROVIDING METHOD, BIO-INFORMATION DATA STORING METHOD AND BIO-INFORMATION DATA TRANSFERRING SYSTEM BASED ON MULTIPLE BLOCKCHAINS

(71) Applicants: MACROGEN, INC., Seoul (KR); Macrogen Corp., Rockville, MD (US)

(72) Inventors: Sungwoo Yang, Bucheon-si (KR); Jaekyung Chon, Seoul (KR); Ik Jung Choi, Seoul (KR); Hyun Min Park, Seoul (KR); Jieun Park, Seoul (KR); Jeongsun Seo, Seoul (KR); Changhoon Kim, Gwangmyeong-si (KR)

(73) Assignees: MACROGEN, INC., Seoul (KR); Macrogen Corp., Rockville, MD (US)

( * ) Notice: Subject to any disclaimer, the term of this patent is extended or adjusted under 35 U.S.C. 154(b) by 0 days.

(21) Appl. No.: 16/221,829

(22) Filed: Dec. 17, 2018

(65) Prior Publication Data

US 2019/0253253 A1    Aug. 15, 2019

(30) Foreign Application Priority Data

Feb. 13, 2018    (KR) .................. 10-2018-0017378

(51) Int. Cl.
*H04L 9/32*    (2006.01)
*G16H 10/60*    (2018.01)
(Continued)

(52) U.S. Cl.
CPC ........ *H04L 9/3242* (2013.01); *G06F 21/6245* (2013.01); *G06F 21/64* (2013.01);
(Continued)

(58) Field of Classification Search
None
See application file for complete search history.

(56) References Cited

U.S. PATENT DOCUMENTS 9,204,405 B2 * 12/2015 Hildebrandt .......... H04W 56/00
9,256,761 B1 *  2/2016 Sahu ..................... G06F 16/21
(Continued)

FOREIGN PATENT DOCUMENTS

JP    2017-220710 A    12/2017
KR    10-2009-0102943 A    10/2009
(Continued)

OTHER PUBLICATIONS

Singh et al., "Practical Personalized Genomics in the Encrypted Domains", Apr. 2018.*
(Continued)

*Primary Examiner* — Piotr Poltorak
(74) *Attorney, Agent, or Firm* — Paratus Law Group, PLLC

(57) ABSTRACT

Disclosed is a method of providing bio-information data based on a plurality of blockchains. The method includes enabling a user blockchain node to store user block data including user information, a shared key, and a hash key for each user of a plurality of users, enabling an electronic contract blockchain node to store contract block data including contract information for a first user requesting a second user to generate bio-information data, the first user and the second user being included in the plurality of users, enabling a data transfer blockchain node to store transfer block data including storage information for at least one storage server that stores the bio-information data, and delivering the transfer block data from the data transfer blockchain node to the first user.

19 Claims, 23 Drawing Sheets

(51) Int. Cl.
  *G06F 21/62* (2013.01)
  *G16B 20/00* (2019.01)
  *G06F 21/64* (2013.01)
  *H04L 9/06* (2006.01)

(52) U.S. Cl.
  CPC ............ *G16B 20/00* (2019.02); *G16H 10/60* (2018.01); *H04L 9/0618* (2013.01); *H04L 9/3239* (2013.01); *H04L 2209/38* (2013.01)

(56) References Cited

U.S. PATENT DOCUMENTS

| | | | | |
|---|---|---|---|---|
| 10,102,526 | B1* | 10/2018 | Madisetti | H04L 9/3239 |
| 10,135,835 | B1* | 11/2018 | Kandel | H04L 63/0876 |
| 10,146,792 | B1* | 12/2018 | Dobrek | G06Q 20/3829 |
| 10,164,779 | B2* | 12/2018 | Uhr | H04L 63/0823 |
| 10,333,696 | B2* | 6/2019 | Ahmed | H04L 9/006 |
| 10,346,815 | B2* | 7/2019 | Glover | G06Q 20/065 |
| 2015/0206106 | A1* | 7/2015 | Yago | G06Q 20/0658 |
| | | | | 705/68 |
| 2015/0332283 | A1* | 11/2015 | Witchey | G06Q 30/018 |
| | | | | 705/3 |
| 2016/0072800 | A1* | 3/2016 | Soon-Shiong | H04L 63/0861 |
| | | | | 726/7 |
| 2016/0300223 | A1* | 10/2016 | Grey | G06Q 20/3825 |
| 2016/0300234 | A1* | 10/2016 | Moss-Pultz | G06F 21/10 |
| 2016/0379213 | A1* | 12/2016 | Isaacson | G06Q 20/12 |
| | | | | 705/44 |
| 2017/0005804 | A1* | 1/2017 | Zinder | H04L 9/3247 |
| 2017/0011460 | A1* | 1/2017 | Molinari | G06Q 40/04 |
| 2017/0132630 | A1* | 5/2017 | Castinado | G06Q 20/4014 |
| 2017/0134161 | A1* | 5/2017 | Goeringer | H04L 9/3236 |
| 2017/0155515 | A1* | 6/2017 | Androulaki | G06F 21/64 |
| 2017/0262862 | A1* | 9/2017 | Aljawhari | G06F 16/242 |
| 2017/0316162 | A1* | 11/2017 | Wall Warner | G16H 10/60 |
| 2017/0344988 | A1* | 11/2017 | Cusden | H04L 9/3247 |
| 2018/0018590 | A1* | 1/2018 | Szeto | G06F 21/6254 |
| 2018/0060496 | A1* | 3/2018 | Bulleit | G16H 10/60 |
| 2018/0082024 | A1* | 3/2018 | Curbera | H04L 9/3236 |
| 2018/0130050 | A1* | 5/2018 | Taylor | G06Q 20/3674 |
| 2018/0130556 | A1* | 5/2018 | Dobai | G06Q 10/10 |
| 2018/0174122 | A1* | 6/2018 | Mattingly | G06Q 30/0631 |
| 2018/0181309 | A1* | 6/2018 | Miyamae | G06F 3/065 |
| 2018/0218176 | A1* | 8/2018 | Voorhees | H04L 9/3239 |
| 2018/0260522 | A1* | 9/2018 | Bitter | G16B 20/00 |
| 2018/0285810 | A1* | 10/2018 | Ramachandran | G06Q 10/087 |
| 2018/0309581 | A1* | 10/2018 | Butler | H04L 9/3247 |
| 2019/0025280 | A1* | 1/2019 | Kaditz | G01N 33/48792 |
| 2019/0026425 | A1* | 1/2019 | Downs | G06Q 20/06 |
| 2019/0130399 | A1* | 5/2019 | Wright | G06F 21/645 |
| 2019/0147431 | A1* | 5/2019 | Galebach | G06Q 20/24 |
| | | | | 705/44 |
| 2019/0198144 | A1* | 6/2019 | Blackley | G16H 20/10 |

FOREIGN PATENT DOCUMENTS

| | | | | |
|---|---|---|---|---|
| KR | 10-1590076 B1 | 2/2016 | | |
| KR | 10-1720268 B1 | 3/2017 | | |
| KR | 10-1763827 B1 | 8/2017 | | |
| WO | WO-2016036969 A1 * | 3/2016 | ......... | H04L 63/0861 |
| WO | WO 2017/087769 A1 | 5/2017 | | |
| WO | WO 2017-091730 A2 | 6/2017 | | |

OTHER PUBLICATIONS

Japanese Office Action for related JP Application No. 2018-231811 dated Apr. 2, 2019 from Japanese Intellectual Property Office.
Stucco Kenni, "Bitcoin Study Session (Technology) Session 1 Understanding Bitcoin Technically (Publication version)", online, Fuji Xerox Co., Ltd., Jun. 2, 2014, pp. 1-68, URL:https://www.slideshare.net/kenjiurushima/20140602-bitcoin1-201406031222.
Korean Office Action for related KR Application No. 10-2018-0017378 dated May 14, 2018 from Korean Patent Office.
Korean Notice of Allowance for related KR Application No. 10-2018-0017378 dated Jul. 11, 2018 from Korean Patent Office.

* cited by examiner

BIO-INFORMATION DATA PROVIDING METHOD, BIO-INFORMATION DATA STORING METHOD AND BIO-INFORMATION DATA TRANSFERRING SYSTEM BASED ON MULTIPLE BLOCKCHAINS

CROSS-REFERENCE TO RELATED APPLICATION

This application claims the benefit under 35 USC 119(a) of Korean Patent Application No. 10-2018-0017378 filed on Feb. 13, 2018, in the Korean Intellectual Property Office, the entire disclosure of which is incorporated herein by reference for all purposes.

BACKGROUND

1. Field

The following description relates to a technique for providing bio-information using blockchains.

2. Description of Related Art

Due to population aging and increases in chronic disease worldwide, the development of health businesses is accelerating.

With the rapid development of medicines and bio-healthcare services, various studies of diseases have allowed incredible progress in genetic diagnosis of several inherited disorders. Specifically on sequencing analysis, Next-Generation Sequencing (NGS) technology has revolutionized almost all fields of biology, agriculture, and medicine, and is widely utilized to analyze genetic variations. For this reason, the studies of genes have become increasingly researched by more people, leading to significant new insights. In particular, studies related to data analysis, disease diagnosis, and new medicine development based on analysis of a large amount of data are going well. Due to increased accessibility of genomic information, a healthcare paradigm is changing from treatment to prevention. The field of healthcare based on genomic information is becoming industrialized in earnest.

Recognizing the important value of genomic data, many countries such as the United States, the United Kingdom, and China are carrying out government-led large-scale international and national genome sequencing projects, such, 1000 Genome Project, US Precision Medicine Initiative, the Genomics England, UK millennium cohort study, and the Chinese millennium Omics Database Project are underway.

Since high-quality genomic data serves as an important control for medical research and population-oriented clinical and drug application, results of the projects noted above may be useful in deriving scientific insights related to individual variability in genes, environment, and lifestyle. This approach can allow medical doctors and researchers to predict more accurately which treatment and prevention strategies for a particular disease will work in which groups of people, and may be referred to as "Precision Medicine" or "Personal Medicine".

Personalized healthcare based on genomic big data is at the core of precision medicine. Precision medicine may refer to a type of personalized medicine that considers genetic, environmental, and biological characteristics of an individual (patient) at all stages from diagnosis to treatment. By using precision medicine, it may be possible to derive an appropriate treatment method by analyzing big data accumulated from various information sources related to a lifestyle and an environment of an individual (patient), as well as medical information.

Personal health information, including medical information, is not necessarily stored through only a single platform, but may also be accumulated through various devices and services. Accordingly, interoperability between the accumulated pieces of information is an important factor in using big data. Thus, many countries are also investing in and supporting policies related to big data. For the United States, the Office of the National Coordinator for Health Information Technology (ONC) was installed to establish a healthcare data sharing environment on the national level. The Health Data Initiative, which is a national medical big data project, was promoted, and also related laws were enacted to encourage the user of big data to share medical records with the patient's content. For the United Kingdom, the Health and Social Care Information Centre (HSCIC) was established, and a strategy to improve health through data utilization, which is called "Power of Information," has been advanced.

Genomic data, which is a piece of healthcare big data, is genomic information unique to each individual. Accordingly, the genomic data should be expanded through data accumulation. Building big data through the sharing of genomic data is very important even for the realization of precision medicine. However, the sharing of genomic data has brought new challenges related to protecting the data.

Genomic data may be utilized in various fields such as Direct-To-Customer (DTC) for general health care, prenatal testing to identify genetic diseases, genetic identification for crime investigation and paternity identification, and disease treatment through an intestinal microorganism genome analysis. Furthermore, genomic data may be used to acquire biological resources, develop useful biomaterials, and preserve and restore endangered species.

Genomic data will be increasingly important and usable as research on genomic data is conducted not only in biological research and medical fields but also in a variety of fields such as ecology and anthropology.

Genomic data may be used to predict not only the present but also the future of a particular individual, and suggests family genetic information of that individual. That is, genomic data may provide a blue-print of an individual's life. For this reason, there is a greater likelihood of privacy breaches and security risks related to genomic data compared to other data.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to an embodiment of the disclosure, there is provided a method of providing bio-information data based on a plurality of blockchains, the method including enabling a user blockchain node to store user block data including user information, a shared key, and a hash key for each user of a plurality of users, enabling an electronic contract blockchain node to store contract block data including contract information for a first user requesting a second user to generate bio-information data, the first user and the second user being included in the plurality of users, enabling a data transfer blockchain node to store transfer block data including storage information for at least one storage server that stores the bio-information data, and delivering the transfer block data from the data transfer blockchain node to the first user.

According to an embodiment of the disclosure, there is provided a method of storing bio-information data based on a plurality of blockchains, the method including enabling a user blockchain node to store user block data including user information, a shared key, and a hash key for each user of a plurality of users, enabling a storage server to store bio-information data that is requested by a first user and generated by a second user, the first user and the second user being included in the plurality of users, and enabling a data transfer blockchain node to store transfer block data including storage information of the storage server that stores the bio-information data.

According to an embodiment of the disclosure, there is provided a system for transferring bio-information data based on a plurality of blockchains, the system including a user blockchain node configured to store user block data including user information, a shared key, and a hash key for each user of a plurality of users, an electronic contract blockchain node configured to store contract block data including contract information for a first user requesting a second user to generate bio-information data, the first user and the second user being included in the plurality of users, a storage server configured to store the bio-information data generated by the second user, and a data transfer blockchain node configured to store transfer block data including storage information for the storage server. The user block data, the control block data, and the transfer block data may be generated by at least one of the first user or the second user.

Figure 1:
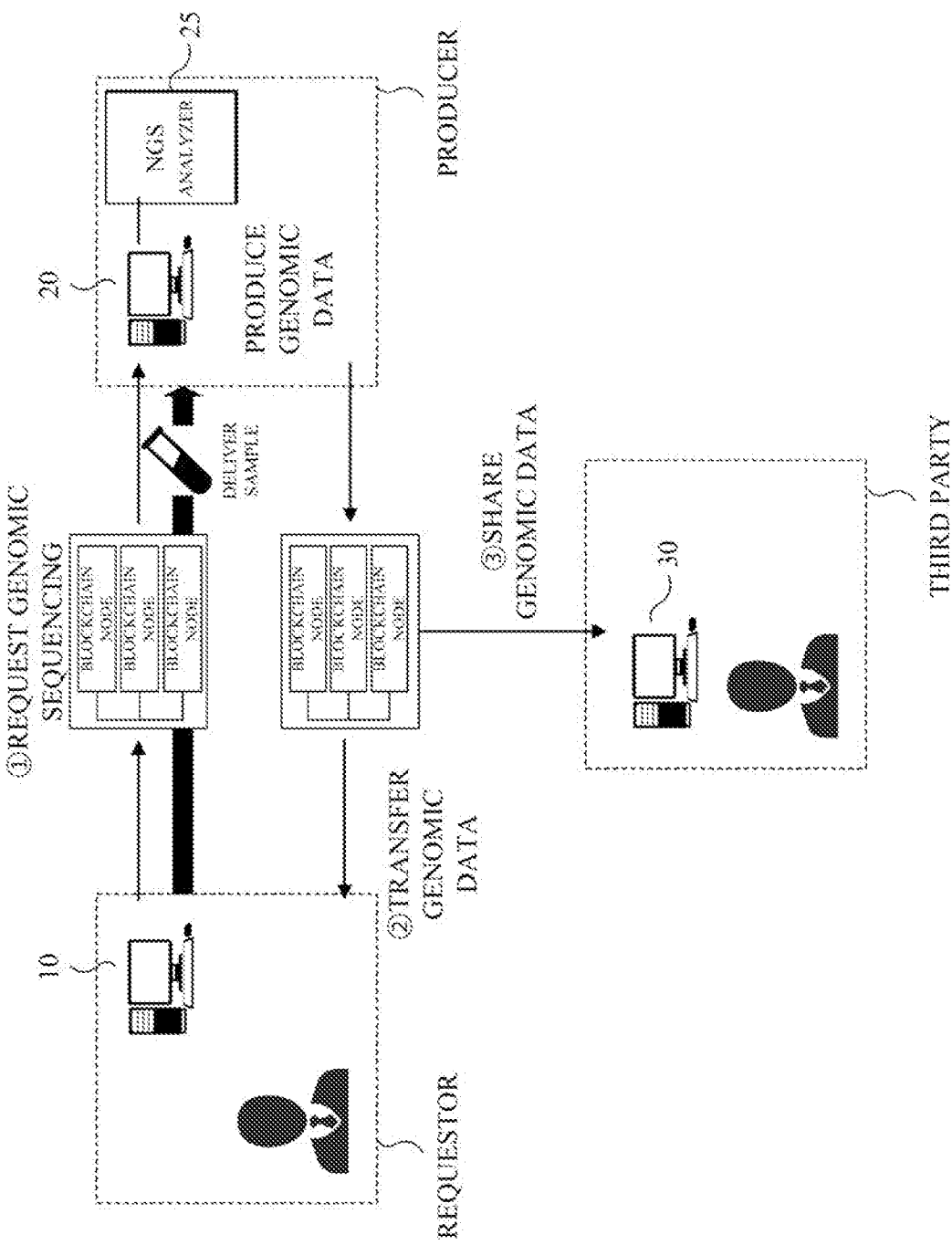
FIG. 1 illustrates an example of genomic data transfer model.

Throughout the drawings and the detailed description, unless otherwise described, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following technology is associated with a data provision service. The following description focuses on bio-information data, but the following technology may be applied to various data provision services irrespective of the type of data.

Terms used herein will be described below.

Genomic data refers to data that is obtained from organisms (humans, animals, microorganisms, etc.) and samples of a specific user. For example, the genomic data may be obtained from a nucleotide sequence, gene expression data, a genetic variation in standard genomic data, DNA methylation, etc., which may be obtained from deoxyribonucleic acid (DNA), ribonucleic acid (RNA), or protein acquired from cells, tissues, or the like. Generally, the genomic data includes sequence information obtained by analyzing a specific sample. The genomic data may be generally represented as digital data. The genomic data includes sequence data obtained through a next generation sequencing (NGS) analyzer or the like.

Genomic analysis data, or simply analysis data, refers to information obtained by analyzing genomic data. For example, the analysis data includes diagnosis results, disease prediction results, degrees of disease risk, disease treatment means, new medicines, and the like which may be acquired by analyzing the genomic data.

Bio-information data refers to genomic data originating from an organism and analysis data. For example, the bio-information data includes DNA base sequences, protein amino acid sequences, protein structure data, gene expression information, protein expression data, gene analysis results, and the like.

Metadata may be data that is derived from a bio-information data producing process and corresponds to data that additionally describes or specifies bio-information data. For example, the metadata for the bio-information data may include genomic data formats, genomic data production methodology, base sequencing apparatus information, sample information, molecular biology technology definitions, an amount of production, an accuracy analysis and statistics on data, a production date, etc.

A requestor refers to a user who requests production of bio-information data. A producer refers to a user who produces bio-information data. A third party refers to a user other than a requestor and a producer. A third party may be a user with whom the bio-information data generated by a producer is shared.

A user terminal or a terminal, which may be a computer device, refers to a client device that is used by a user. The user refers to a specific entity such as a person or an institute, but may be specified as a user terminal in a system.

The computer device refers to a device that analyzes input source data using a computing device such as a central processing unit (CPU), an application processor (AP), etc. Generally, the computer device may include a computing device, a memory, an input/output device, a communication interface device, and the like. The computer device may be implemented as a device such as a server, a personal computer (PC), a tablet PC, a smartphone, and the like.

A hash key may be a value that is used to identify a user over a blockchain network. The hash key may be generated in various ways. Representative hash key generation algorithms may include MD5, SHA-256, and the like. The hash key may be a value that is unique to a specific user. The hash key may be a key that is composed of character strings of various lengths.

A public key and an encryption key may be keys for encrypting and transferring data over a blockchain network. The public key and the encryption key may be used for so-called public key type encryption. The public key may be a key for encrypting data, and the encryption key may be a key for decrypting encoded data. The public key and the encryption key may be paired and may be randomly generated using various public key encryption schemes (e.g., Rivest-Shamir-Adleman (RSA), elliptic curve cryptography, etc.).

A blockchain may refer to a chain-based distributed data storage environment in which small pieces of data, each of which is called a block, are generated by a peer-to-peer (P2P) network as data to be managed. A blockchain network refers to network elements constituting a blockchain.

FIG. 1 illustrates an example of genomic data transfer model. FIG. 1 is a model for generating and transferring genomic data, which is a piece of bio-information data. A requestor requests genome sequencing from a producer. The sequencing request corresponds to a contract between the two parties. The requestor may request the genome sequencing through a user terminal 10, and the producer may accept the sequencing request through a user terminal 20. In this case, the contract between the requestor and the producer is performed through a blockchain.

The requestor delivers a sample to be analyzed to the producer. The producer generates genomic data using an NGS analyzer 25. The producer may store the genomic data and information regarding the genomic data generated through the user terminal 20 in a blockchain in the form of block data. The producer may receive the genomic data generated through the blockchain by using the user terminal 10.

Furthermore, the requestor or the producer may share the genomic data with a third party by using the blockchain in which the information regarding the genomic data is stored. The third party may receive the generated genomic data by using the user terminal 30.

A blockchain network largely has two elements. One element may be a blockchain node, and the other element may be a client. From a user perspective, the blockchain node serves as a backend of a normal service, and the blockchain client serves as a client. When the client generates a new transaction, the nodes share and execute the transaction through a distributed consensus process. The client may check a result of the transaction. In FIG. 1, the user terminals 10, 20, and 30 correspond to clients. In FIG. 1, the blockchain node corresponds to a separate node (terminal, server, etc.) connected to the network.

Figure 2:
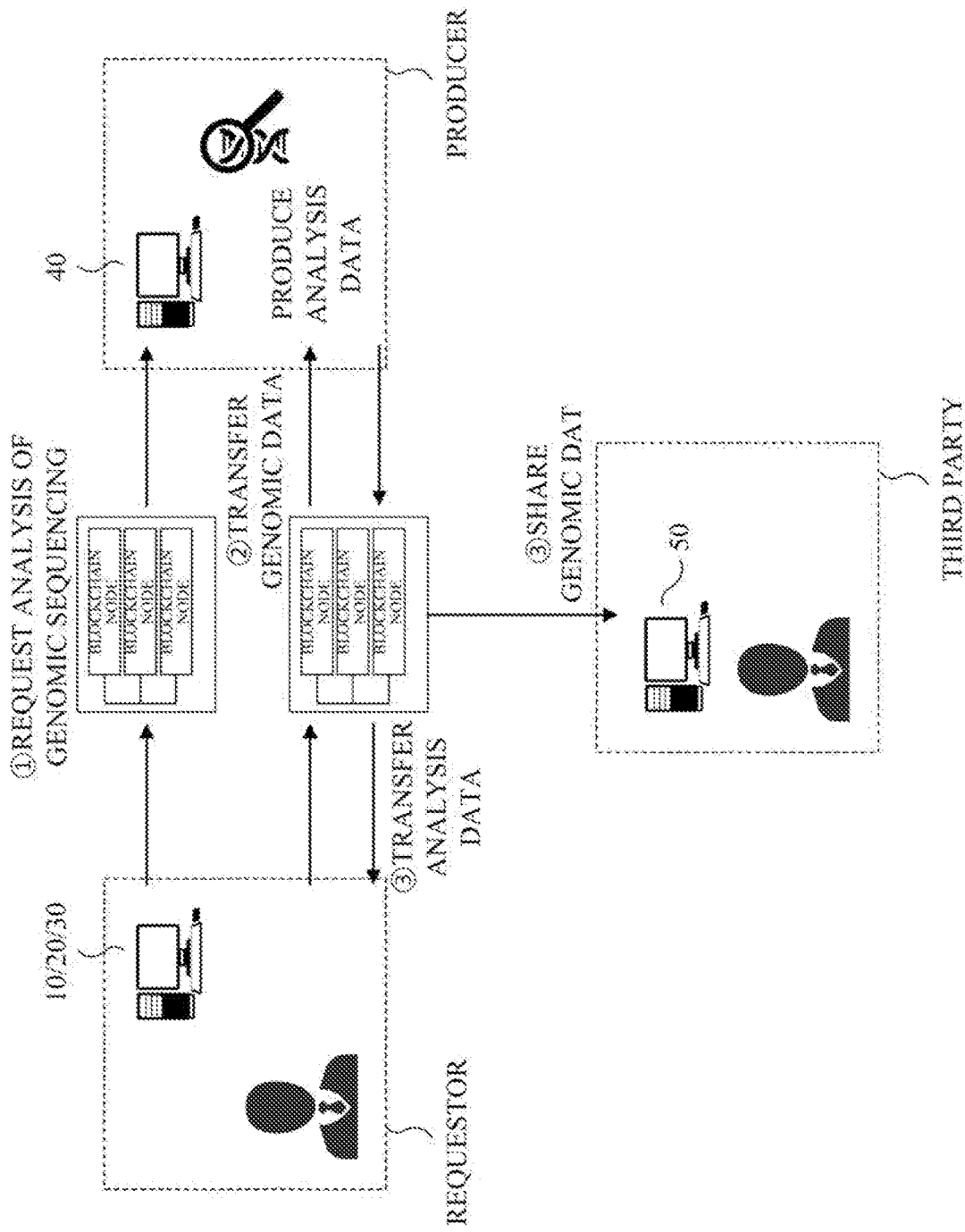
FIG. 2 illustrates an example of genomic analysis data transfer model.

FIG. 2 illustrates an example of genomic analysis data transfer model. FIG. 2 is a model for generating and transferring genomic data, which is a piece of bio-information data. A requestor requests genome data analysis from a producer. The analysis request corresponds to a contract between the two parties. The requestor may request the genome data analysis through the user terminals 10 and 20, and the producer may accept the sequencing request through a user terminal 40. The requestor of FIG. 2 may be the requestor of FIG. 1, the producer of FIG. 1, or the sharer of FIG. 1. In this case, the contract between the requestor and the producer is performed through a blockchain.

The requestor delivers genomic data to be analyzed to the producer through the user terminals 10, 20, and 30. The producer generates analysis data through analysis using software or biological experiments. The producer may store the generated analysis data and information regarding the analysis data through the user terminal 40 in the blockchain in the form of block data. The requestor may receive the generated analysis data through the blockchain by using the user terminals 10, 20, and 30.

Furthermore, the requestor or the producer may share the analysis data with a third party by using the blockchain in which the information regarding the analysis data is stored. The third party may receive the genomic data from the blockchain by using a user terminal 50.

Figure 3:
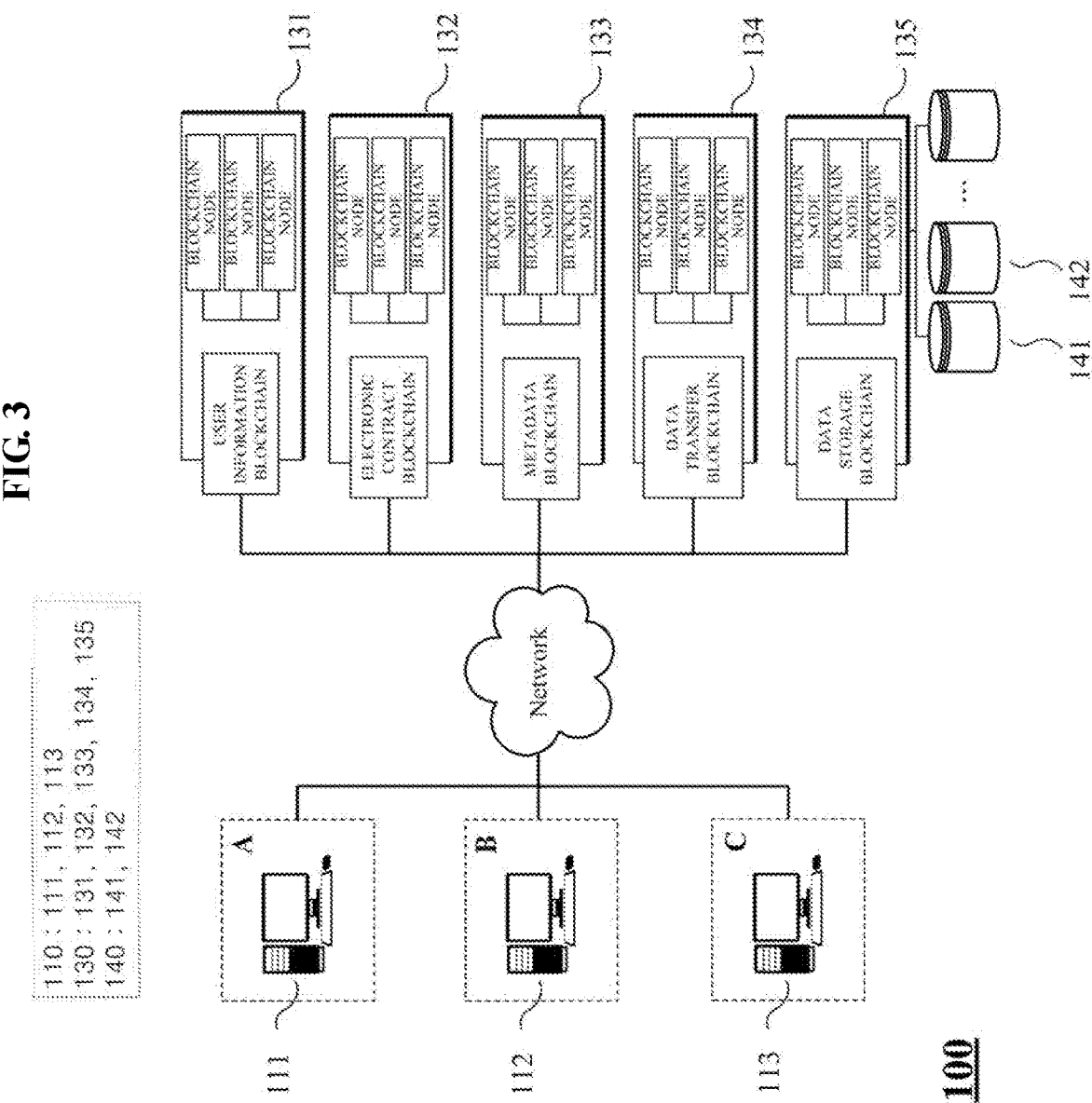
FIG. 3 illustrates an example of bio-information data transfer system.

FIG. 3 illustrates an example of bio-information data transfer system 100. The bio-information data transfer system 100 includes a user terminal 110, a blockchain 130, and a storage server 140.

The user terminal 110 includes a user terminal 111 being used by a requester, a user terminal 112 being used by a producer, and a user terminal 113 being used by a sharer. The user terminal 111 is shown in a region A, the user terminal 112 is shown in a region B, and the user terminal 113 is shown in a region C. At least one user terminal may be present in each region. The user terminal 113 being used by the third party is not an element essential to the system.

FIG. 3 shows a total of five blockchains 131 to 135. One blockchain may be composed of a plurality of blockchain nodes. The five blockchains are as follows.

The user information blockchain 131 holds user-related information. The user information blockchain 131 stores a hash key for the user and personal information for the user. For example, the personal information may include information such as the user's identifier, name, gender, affiliation, and birth date. User block data includes personal information that may be encrypted using a specific public key.

The electronic contract blockchain 132 holds information regarding a contract between users. The user information blockchain 131 holds contract information (requested details) and hash keys of users who participate as contractors. For example, the contract information may include information regarding source data, an analysis method, an analyzer, a due date for analysis, a source data holding period, a data processing method upon the end of a contract, sharer information, etc. The contract block data includes contract information that may be encrypted with a specific public key.

The metadata blockchain 133 holds metadata for the bio-information data. The metadata block data includes metadata that may be encrypted with a specific public key. The metadata may include a data format, a production method, base sequencing apparatus information, sample information, molecular biology technology definitions, an amount of production, a reliability of data, a production date, and the like.

The data transfer blockchain 134 holds hash keys of two users who participate in data transmission/reception and transfer information for a bio-information data file to be transferred. The transfer information may be information that is needed for data transfer. For example, the transfer information may include a file size, a file name, a file location, a verification key, etc. The transfer block data includes transfer information that may be encrypted with a specific public key.

The data storage blockchain 135 holds hash keys of two users who participate in data transmission/reception and storage information for bio-information data located in the storage server. The storage information may be information regarding bio-information data stored in storage servers 141 and 142. For example, the storage information may include the storage servers' identifiers, locations where the bio-information data is stored in storage media of the storage servers, file sizes, file partitioning information, verification keys, etc. The bio-information data may be encrypted with a specific public key and stored in the storage servers. However, fundamentally, the storage block data may store storage information while the storage information is not encrypted.

The storage server 140 may store the bio-information data. The storage server may store the bio-information data in various ways. The storage server may store the bio-information data itself, like typical servers. The storage server may be a single server. Alternatively, as shown in FIG. 3, the storage server 140 may be composed of a plurality of servers 141, 142, and so on. When there are a plurality of storage servers, the bio-information data may be stored in the storage servers in a distributed manner. Furthermore, when there are a plurality of storage servers, one server (a main storage server) may store the generated bio-information data itself, and the other servers (sub-storage servers) may store the bio-information data in a distributed (divided) manner. When a plurality of servers are used, a plurality of storage servers or a plurality of sub-storage servers may serve as nodes constituting a blockchain such that the plurality of storage servers constitute a data storage blockchain.

Figure 4:
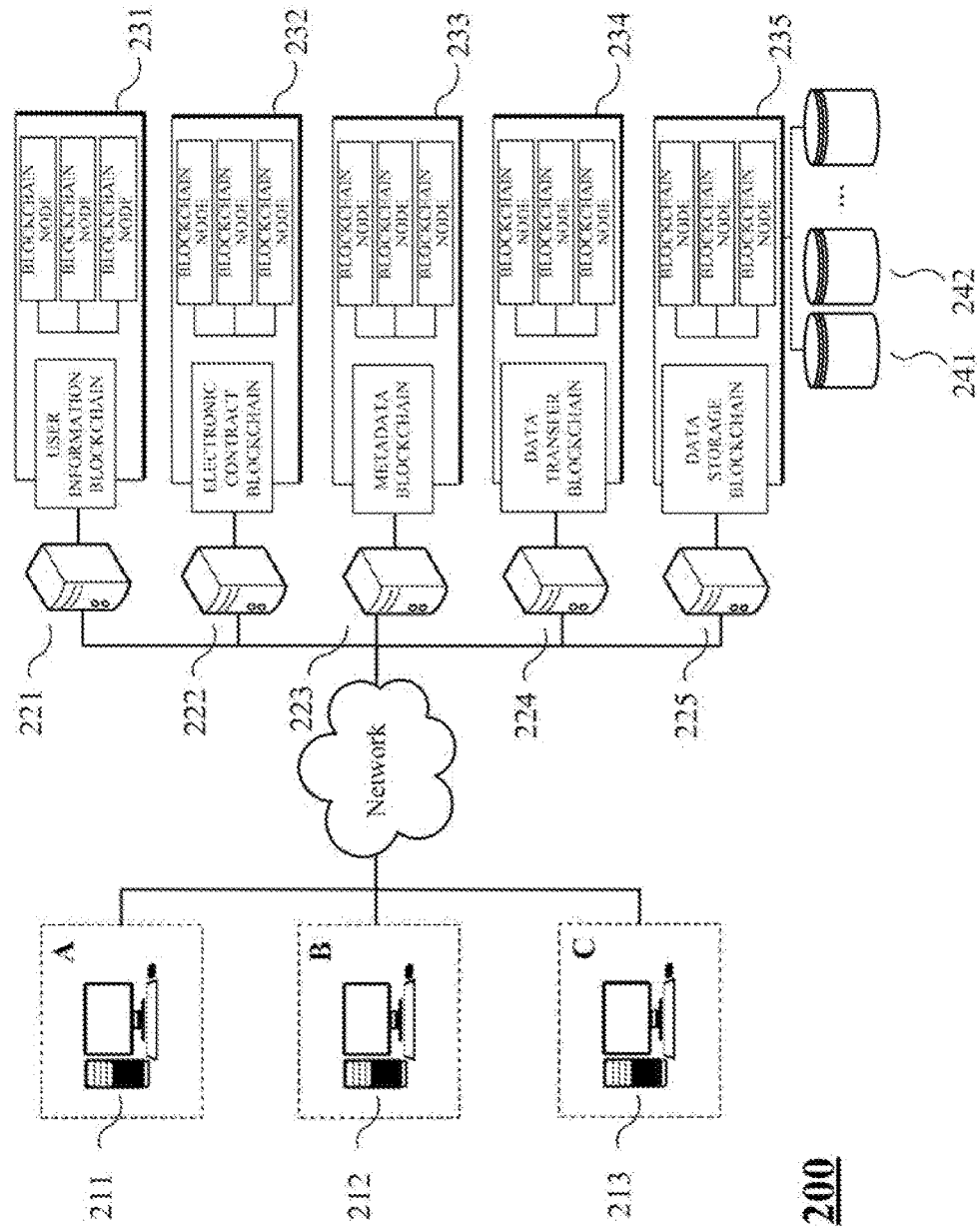
FIG. 4 illustrates another example of bio-information data transfer system.

FIG. 4 illustrates another example of bio-information data transfer system 200. The system 200 of FIG. 4 may include basically the same elements as the system 100 of FIG. 3. However, the system 200 of FIG. 4 includes a registration server 220 that manages blockchains. The bio-information data transfer system 200 includes a user terminal 210 and a blockchain 230 as well as the registration server 220.

The user terminal 210 includes a user terminal 211 being used by a requester, a user terminal 212 being used by a producer, and a user terminal 213 being used by a third party. The user terminal 211 is shown in a region A, the user terminal 212 is shown in a region B, and the user terminal 213 is shown in a region C. At least one user terminal may be present in each region. The user terminal 213 being used by the third party is not an element essential to the system.

FIG. 4 shows a total of five blockchains 231 to 235. One blockchain may be composed of a plurality of blockchain nodes. In FIG. 4, one blockchain is connected to one registration server. Each registration server may generate block data stored in a corresponding blockchain and may register (store) the generated block data. A system or an individual user may compare the block data stored in the registration server to reference block data stored in the blockchain to check data forgery and tampering. The five blockchains may be the same as described in FIG. 3.

In FIG. 4, a registration server is present for each blockchain. The five registration servers 220 are a user registration server 221, an electronic contract registration server 222, a metadata registration server 223, a data transfer registration server 224, and a data storage registration server 225.

The user registration server 221 generates user block data and stores hash keys and user information in the user information blockchain 231. The electronic contract registration server 222 generates contract block data and stores hash keys and contract information in the electronic contract blockchain 132. The metadata registration server 223 generates metadata and stores hash keys and metadata in the metadata blockchain 233. The data transfer registration server 224 generates transfer information and stores hash keys and transfer information in the data transfer blockchain 234. The data storage registration server 225 generates storage information and stores hash keys and storage information in the data storage blockchain 235. The system 200 may include a single registration server or two to five registration servers. Here, the number of registration servers does not represent the number of physical devices, but does represent the number of functional types (types of blockchains being managed).

The storage server stores bio-information data. The storage server may store the bio-information data in various ways. The storage server may store the bio-information data itself, like typical servers. The storage server may be a single server. Alternatively, as shown in FIG. 4, the storage server may be composed of a plurality of servers 242, 242, and so on. When there are a plurality of storage servers, the bio-information data may be stored in the storage servers in a distributed manner. Furthermore, when there are a plurality of storage servers, one server (a main storage server) may store the generated bio-information data itself, and the other servers (sub-storage servers) may store the bio-information data in a distributed (divided) manner. When a plurality of servers are used, a plurality of storage servers or a plurality of sub-storage servers may serve as nodes constituting a blockchain such that the plurality of storage servers constitute a data storage blockchain.

Figure 5:
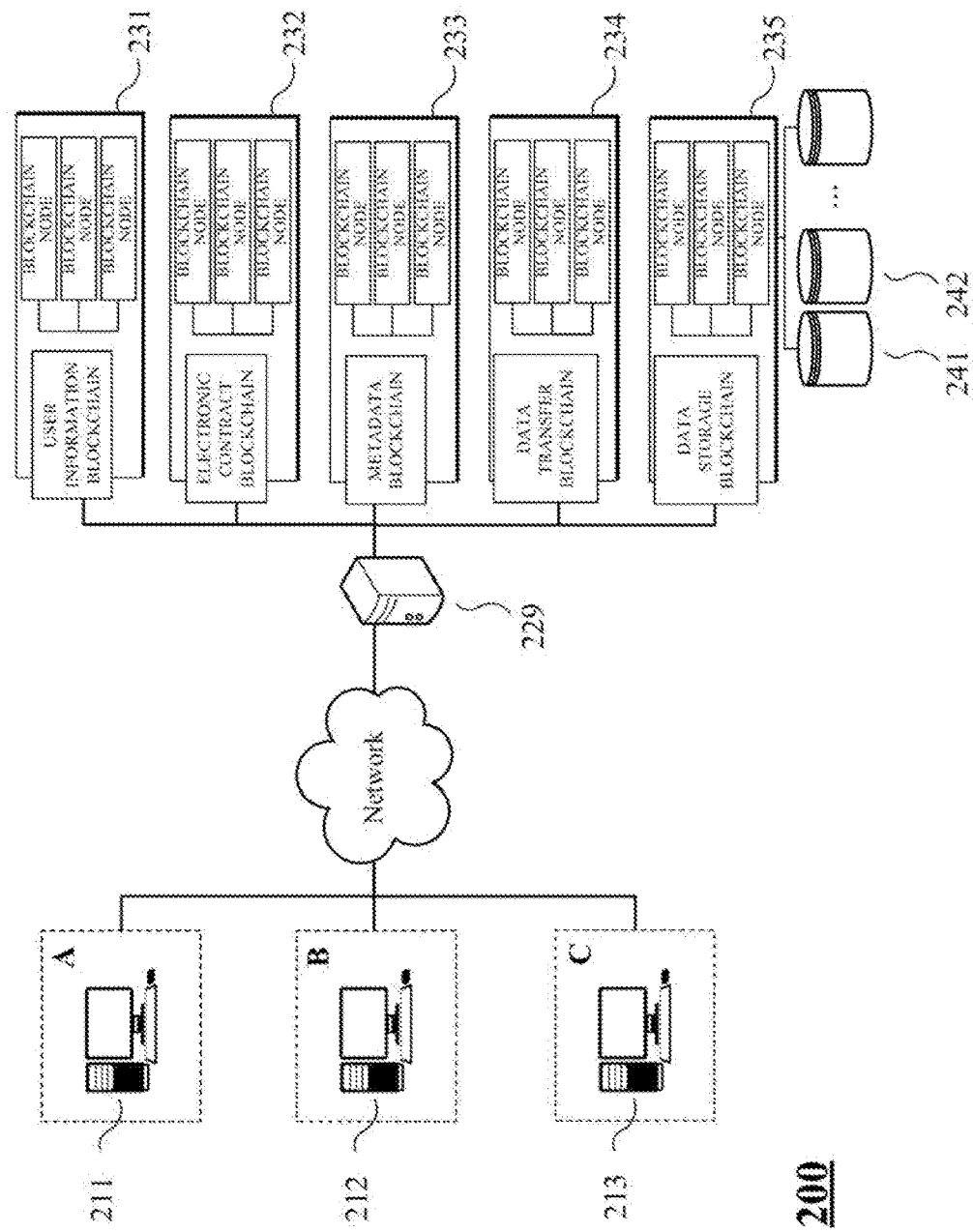
FIG. 5 illustrates still another example of bio-information data transfer system.

FIG. 5 illustrates still another example of bio-information data transfer system 200. The system 200 of FIG. 5 is almost the same as the system 200 of FIG. 4. In the system 200 of FIG. 5, however, one registration server 229 registers block data and manages blockchains. The registration server 229 corresponds to an integrated management server. The other operations may be the same as those of the system 200 of FIG. 4. Unlike FIG. 5, a plurality of registration servers may generate and manage one or more blockchains. For example, one registration server may generate and manage the data storage blockchain and the data transfer blockchain, and the other registration server may generate and manage the other blockchains. The number of registration servers may depend on the implementation of the system 200.

Hereinafter, the registration server refers to the servers having different functions, which were described in FIG. 4, or an integrated management server, which was described in FIG. 5.

Figure 6:
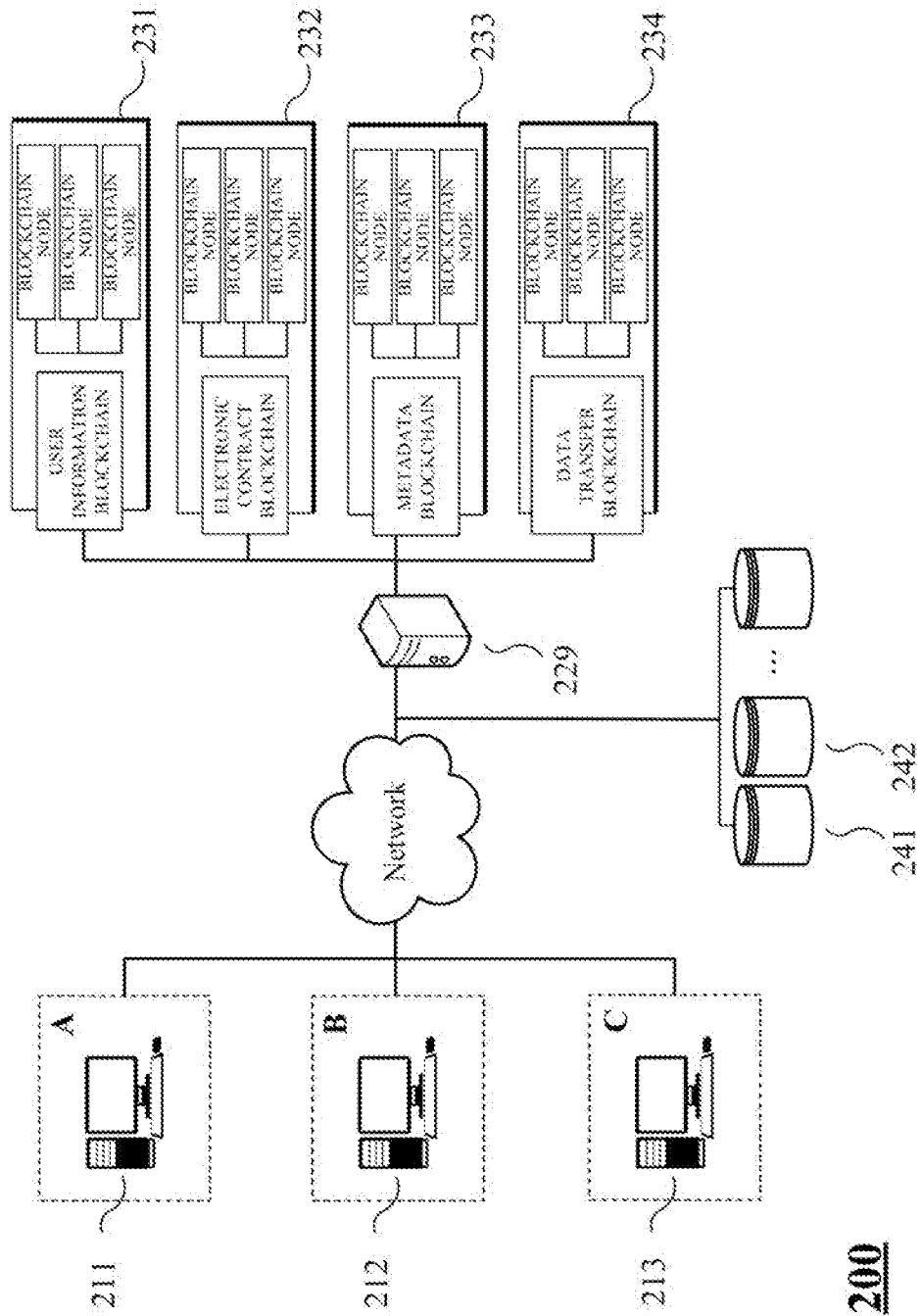
FIG. 6 illustrates still another example of bio-information data transfer system.

FIG. 6 illustrates still another example of bio-information data transfer system 200. The system 200 of FIG. 6 is almost the same as the system 200 of FIG. 5. However, the system 200 of FIG. 6 does not include the data storage blockchain. The system 200 of FIG. 6 is an example in which the bio-information data is stored not in a blockchain form but in a typical storage server. In this case, the transfer information contained by the data transfer blockchain may include the storage servers' identifiers, locations where the bio-information data is stored in storage media of the storage servers, file names, file sizes, file partitioning information, verification keys, etc. That is, the transfer information includes information that may be needed by a user to access the bio-information data stored in the storage servers 241, 242, and so on.

Figure 7:
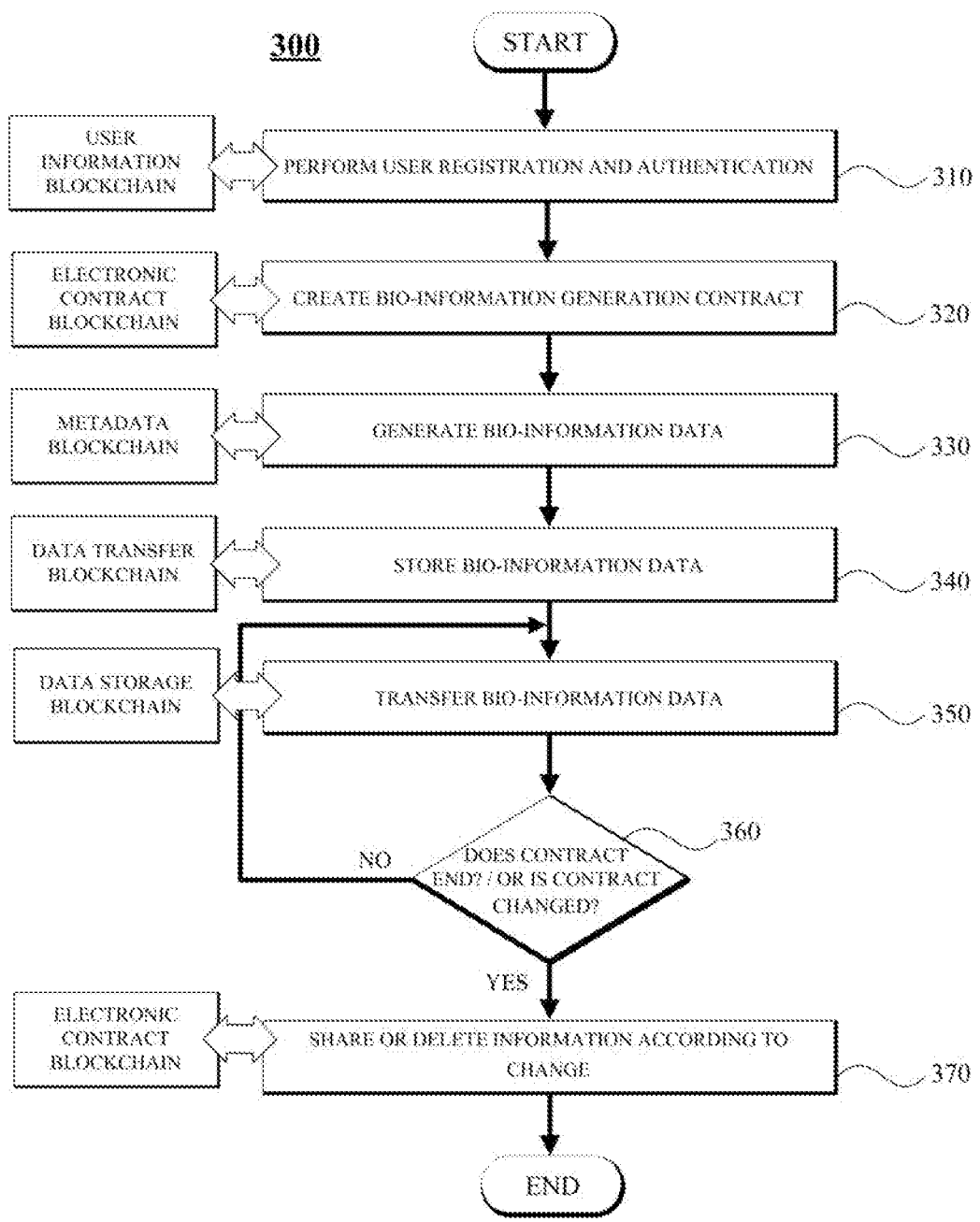
FIG. 7 illustrates an example flowchart of a process in which a bio-information data provision service is proceeding.

FIG. 7 illustrates an example flowchart of a process 300 in which a bio-information data provision service is being executed. FIG. 7 shows a schematic example of the process 300 in which a bio-information data provision service is proceeding.

First, a user registers user information in a system (310). To this end, the user inputs the user information using a user terminal. The user terminal 111, 112, or 113 may generate user block data using user information, encryption keys, and the like and may store the generated user block data in the user information blockchain 231. When a registration server is used, the registration server 221 or 229 may generate user block data using the input user information and may store the generated user block data in the user information blockchain 231. The user may be authenticated using the generated user information blockchain 231. For example, only an authenticated user may be able to proceed to subsequent operations (contract creation, bio-information data transfer, etc.).

In order to receive the biologic information data, a contract should be created between a requestor and a producer. The user terminal 111, 112, or 113 may generate contract block data and store the generated contract block data in the electronic contract blockchain 232. When a registration server is used, the registration server 222 or 229 may generate contract block data using contract information input by the requestor and the producer' signature and may store the generated contract block data in the electronic contract blockchain 232. Thus, a bio-information data provision contract may be created (320).

The producer generates bio-information data (350). The user terminal 112 may generate bio-information data and store the generated bio-information data in the metadata blockchain 233. When a registration server is used, the user terminal 112 may deliver metadata for the generated bio-information data to the registration server 223 or 229. The registration server 223 or 229 may generate metadata block data for the received metadata and may store the generated metadata block data in the metadata blockchain 233. The generation and storage of the metadata for bio-information data may not be essential to this process.

The bio-information data generated by the producer may be stored in a storage server (340). As described above, a plurality of storage servers may store the bio-information data in the form of a blockchain. The user terminal 112 may deliver the generated bio-information data to the storage servers to configure a blockchain. When a registration server is used, the registration server 225 or 229 may generate storage block data using the bio-information data and may store the generated storage block data in the data storage blockchain 235.

The bio-information data should be transferred to the requestor (350). To this end, after the storage blockchain 235 is generated, the user terminal 112 may generate transfer block data including the storage information and may store the generated transfer block data in the data transfer blockchain 234. When a registration server is used, the registration server 224 or 229 may generate transfer block data using the storage information and may store the transfer block data in the data transfer blockchain 234. The requestor may receive the bio-information data through the data transfer blockchain 234 (350).

Subsequently, the system monitors whether the contract ends or is changed (360). When the contract ends or is changed, the registration server 222 or 229 may update the contract if necessary. Subsequently, according to the details of the contract, the stored data may be deleted, and the bio-information data may be shared with a third party (370).

Each operation shown in FIG. 7 will be described below. An embodiment in which the registration server is not involved as with the system 100 of FIG. 3 and an embodiment in which the registration server is involved as with the systems 200 of FIGS. 4 to 6 will be described. The following bio-information data transfer process may be implemented in various forms such as (i) an example in which a registration server is not involved, (ii) an example in which a registration server is involved, and (iii) an example of a combination of some operations in which a registration server is not involved and the other operations in which a registration server is involved.

Figure 8:
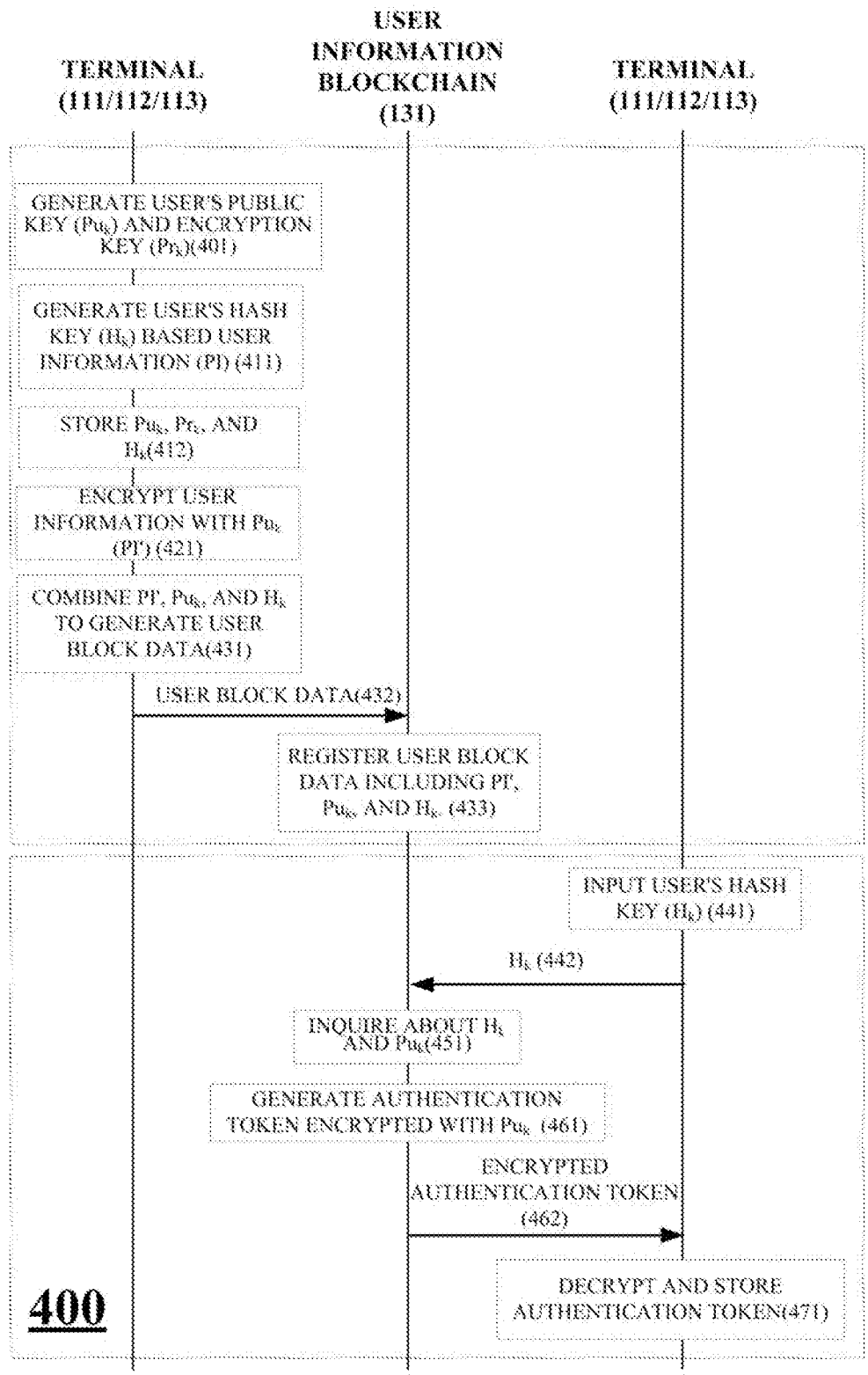
FIG. 8 illustrates an example process of user registration and user authentication.

FIG. 8 illustrates an example process of performing user registration and user authentication (400). FIG. 8 illustrates an example operation of the system 100 of FIG. 3. FIG. 8 shows both of the user registration process and the user authentication process.

The user registration process will be described. In FIG. 8, a terminal refers to the user terminal 111, 112, or 113. First, a user should register with the system in order to request generation of bio-information data, store and transfer the bio-information data, share the bio-information data, etc. The user terminal may generate the user's public key $Pu_k$ and encryption key $Pr_k$ (401). The public key may be used to encrypt certain data (a user's personal information, an electronic contract, bio-information data, etc.), and the encryption key may be used to decrypt data.

The user terminal 111, 112, or 113 generates a hash key $H_k$ on the basis of its own user information PI. Various algorithms or hash functions may be used to generate the hash key. The hash key $H_k$ is used as an identifier of the user (the user terminal) that generates the hash key $H_k$. Accordingly, the hash key $H_k$ corresponds to user-specific unique information. Alternatively, unlike FIG. 8, the user terminal 111, 112, or 113 may transfer its own user information PI to a separate server and may receive a hash key from the server.

The user terminal 111, 112, or 113 stores the user's public key $Pu_k$, the encryption key $Pr_k$, and the hash key $H_k$ in a storage medium (412).

The user terminal 111, 112, or 113 encrypts the user information PI with the user's public key $Pu_k$ to generate the encrypted user information PI' (421). The user terminal 111, 112, or 113 combines the encrypted user information PI', the user's public key $Pu_k$, and the hash key $H_k$ to generate user block data (431). The user terminal 111, 112, or 113 may deliver the generated user block data to the user registration server 221 (432). The user information blockchain 131 registers the user block data including the encrypted user information PI', the user's public key $Pu_k$, and the hash key H$_k$ (433). The above-described operations 401 to 433 correspond to the user information registration process.

Now, the user authentication process will be described. The user authentication may be needed for each or a specific step of the bio-information data provision service. Only a user authenticated through the user authentication may be able to proceed to subsequent steps. When a user is successfully authenticated, the user may acquire information (a public key, an encryption key, or a hash key) regarding another user through the user information blockchain 131.

A user who needs authentication inputs his/her own hash key H$_k$ into the user terminal 111, 112, or 113 (441). The input hash key H$_k$ may be transferred to the user information blockchain 231 (442). The user information blockchain 131 inquires about the user's public key Pu$_k$ on the basis of the input hash key H$_k$ (451). The user information blockchain 131 generates an authentication token and encrypts the authentication token with the user's public key Pu$_k$ (461). The user information blockchain 131 transfers the encrypted authentication token to the user terminal 111, 112, or 113 having the hash key H$_k$ (462). The user terminal 111, 112, or 113 decrypts and stores the received authentication token (471). Subsequently, the user terminal 111, 112, or 113 may use the authentication token while communicating with the blockchain. The blockchain that requires authentication may provide specific data to only a user terminal that delivers a valid authentication token.

Figure 9:
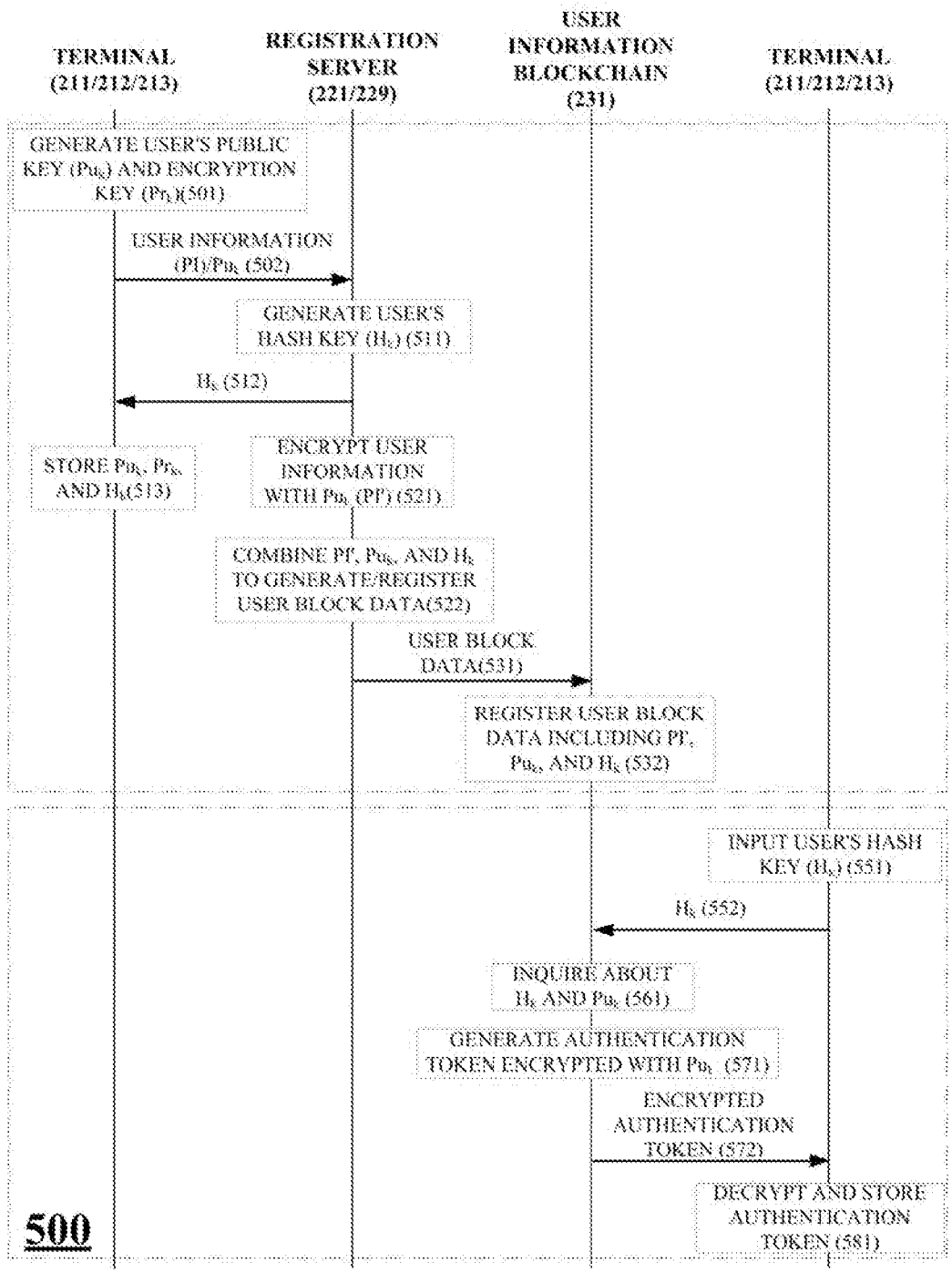
FIG. 9 illustrates another example process of performing user registration and user authentication.

FIG. 9 illustrates another example process 500 of performing user registration and user authentication. FIG. 9 illustrates an example operation of the system 200 of FIG. 4 or 5. FIG. 9 shows both of the user registration process and the user authentication process.

The user registration process will be described. In FIG. 9, a terminal refers to the user terminal 211, 212, or 213. First, a user should register with the system in order to request generation of bio-information data, store and transfer the bio-information data, share the bio-information data, etc. The user terminal may generate the user's public key Pu$_k$ and an encryption key Pr$_k$ (501). The public key may be used to encrypt certain data (a user's personal information, an electronic contract, genomic data, bio-information data, etc.), and the encryption key may be used to decrypt data.

The user registration server 221 may generate a hash key. The user terminal 211, 212, or 213 delivers its own public key Pu$_k$ to the user registration server 221 in addition to its own user information PI (502). The user registration server 221 generates the hash key H$_k$ for the user who has requested generation of the hash key on the basis of the user information PI (511). The hash key H$_k$ is used as an identifier of the user (the user terminal) that requests the hash key H$_k$. Accordingly, the hash key H$_k$ corresponds to user-specific unique information. The user registration server 221 generates the hash key H$_k$ by inputting the user information PI to a certain hash function. Various algorithms or hash functions may be used to generate the hash key. The user registration server 221 delivers the generated hash key H$_k$ to the user terminal 211, 212, or 213 that requests the hash key (512). The user terminal 211, 212, or 213 that requests the hash key stores the user's public key Pu$_k$, the encryption key Pr$_k$, and the hash key H$_k$ in a storage medium (513).

The user registration server 221 encrypts the user information PI with the user's public key Pu$_k$ to generate the encrypted user information PI' (521). The user registration server 221 combines the encrypted user information PI', the user's public key Pu$_k$, and the hash key H$_k$ to generate user block data (522). The user registration server 221 may register the generated user block data (522).

The user registration server 221 delivers the generated user block data to the user information blockchain 231 (531). The user information blockchain 231 registers the user block data including the encrypted user information PI', the user's public key Pu$_k$, and the hash key H$_k$ (532). The above-described operations 501 to 532 correspond to the user information registration process.

Subsequently, it may be checked whether the user information is forged or tampered. The user, or another entity (a server in the system or an external server for forgery and tampering check), may check whether the user information is changed by comparing corresponding block data registered in the user registration server 221 to the reference block data stored in the user information blockchain 231.

Now, the user authentication process will be described. The user authentication may be needed for each, or a specific step, of the bio-information data provision services. Only a user authenticated through the user authentication may be able to proceed to subsequent steps. When a user is successfully authenticated, the user may acquire information (a public key, an encryption key, or a hash key) regarding another user through the user information blockchain 231.

A user who needs authentication inputs his/her own hash key H$_k$ into the user terminal 211, 212, or 213 (551). The input hash key H$_k$ may be transferred to the user information blockchain 231 (552). The user information blockchain 231 inquires about the user's public key Pu$_k$ on the basis of the input hash key H$_k$ (561). The user information blockchain 231 generates an authentication token and encrypts the generated authentication token with the user's public key Pu$_k$ (571). The user information blockchain 231 transfers the encrypted authentication token to the user terminal 211, 212, or 213 having the hash key H$_k$ (572). The user terminal 211, 212, or 213 decrypts and stores the received authentication token (581). Subsequently, the user terminal 211, 212, or 213 may use the authentication token while communicating with the blockchain. The blockchain that requires authentication may provide specific data to only a user terminal that delivers a valid authentication token.

Figure 10:
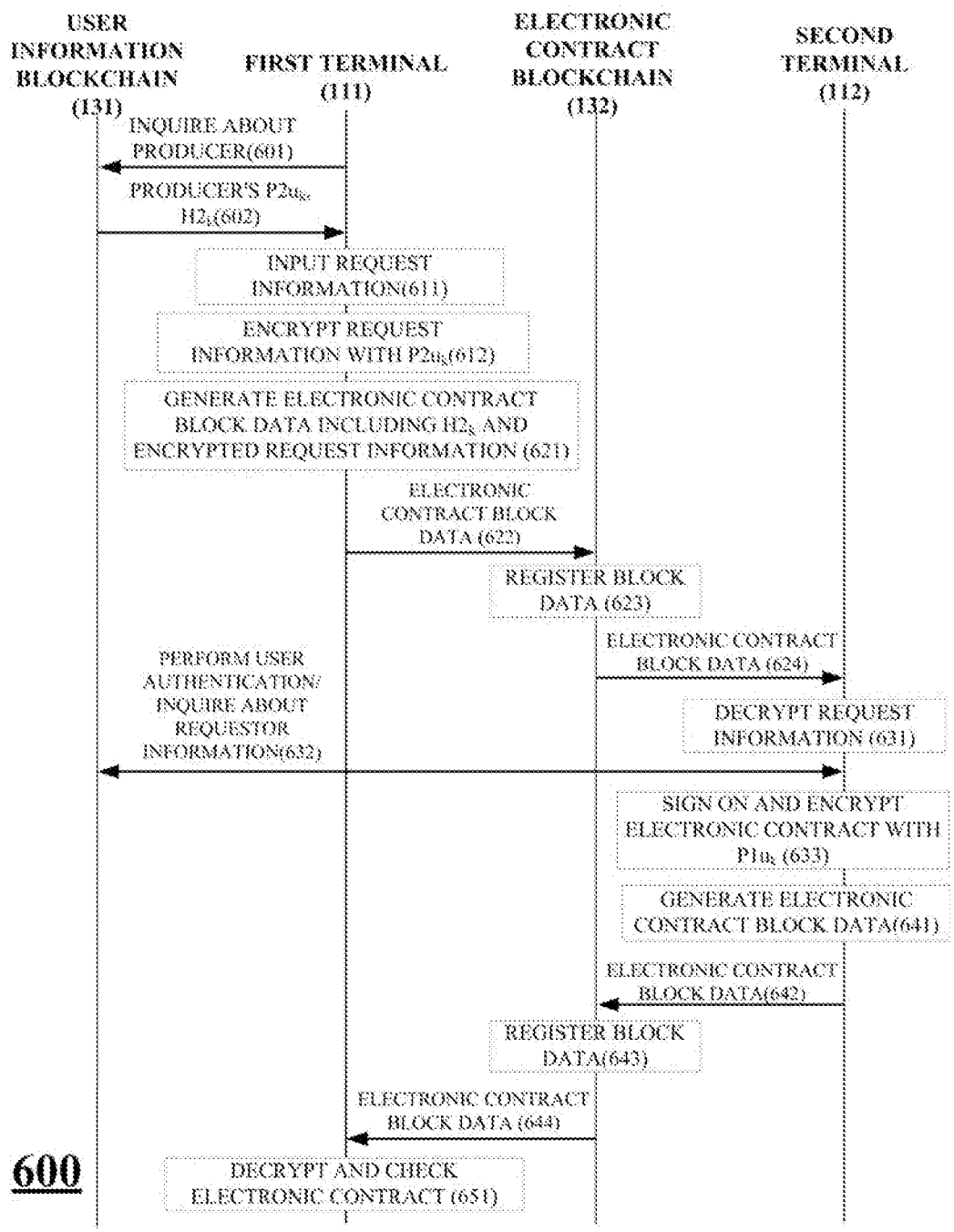
FIG. 10 illustrates an example process of establishing a bio-information data contract.

FIG. 10 illustrates an example process 600 of establishing a bio-information data contract. FIG. 10 illustrates an example operation of the system 100 of FIG. 3. FIG. 10 is an example contract for a bio-information data production request between a requestor and a producer. Among user terminals in FIG. 10, a terminal 111 corresponding to the requestor is represented as a first terminal 111, and a terminal 112 corresponding to the producer is represented as a second terminal 112. It is assumed that the first terminal 111 and the second terminal 112 pre-registered their user information.

The first terminal 111 performs user authentication using the user information blockchain 131. When the authentication is successful, the first terminal 111 inquires of the user information blockchain 131 about the producer on the basis of information (user information) regarding the producer (601). The first terminal 111 receives the producer's public key P2u$_k$ and hash key H2$_k$ from the user information blockchain 131 (602).

The first terminal 111 inputs request information (611). The request information refers to all information for generating bio-information data. For example, the request information may include at least one of genome sample information, bio-information data, library information for base sequencing, an analysis date, an analysis method, an analyzer condition, and requestor information. The first terminal 111 encrypts the request information with the public key P2u$_k$ (612).

The first terminal 111 generates electronic contract block data including the hash key $H2_k$ and the encrypted request information (621). The first terminal 111 delivers the generated electronic contract block data to the electronic contract blockchain 132 (622). The electronic contract blockchain 132 registers the electronic contract block data including the encrypted request information and the hash key $H2_k$ (623).

The electronic contract blockchain 132 transfers the electronic contract block data including the request information to the second terminal 112 on the basis of the hash key $H2_k$ (624). The second terminal 112 decrypts the request information included in the block data with its own encryption key (631).

The second terminal 112 may perform user authentication through the user information blockchain 131 (632). When the authentication is successful, the second terminal 112 may inquire of the user information blockchain 131 about the requestor's public key $P1u_k$ and hash key $H1_k$ and may receive the public key $P1u_k$ and the hash key $H1_k$ from the user information blockchain 131 (632). Meanwhile, the request information may pre-include the requestor's public key $P1u_k$ and hash key $H1_k$. Even for the latter case, the second terminal 112 may proceed to a signing step only when the authentication is successful.

The producer checks the request information decrypted with an encryption key that may be symmetric to the requestor's public key and signs on the electronic contract (633). The signature corresponds to verification of user authentication information and transaction approval for the producer. The second terminal 112 encrypts (i) the request information or (ii) the request information and the signature with the requestor's public key $P1u_k$ (633). The final electronic contract may include the requestor's hash key $H1_k$, the producer's hash key $H2_k$, the request information encrypted with the requestor's public key $P1u_k$, and the producer's signature key. The second terminal 112 generates electronic contract block data including the requestor's hash key $H1_k$, the producer's hash key $H2_k$, the request information encrypted with the requestor's public key $P1u_k$, and the producer's signature key (641). The second terminal 112 delivers the generated electronic contract block data to the electronic contract blockchain 132 (642). The electronic contract blockchain 132 registers the electronic contract block data (643).

Subsequently, it may be checked whether the electronic contract is forged or tampered. The user or another entity (a server in the system or an external server for forgery and tampering check) may check whether the electronic contract is changed by comparing corresponding block data registered in the electronic contract registration server 122 to the reference block data stored in the electronic contract blockchain 132.

The electronic contract blockchain 132 may deliver the electronic contract to the first terminal 111 on the basis of the requestor's hash key $H1_k$ (644). The first terminal 111 may decrypt the request information/signature included in the received electronic contract with its own encryption key and may check the details of the contract and the approval (651).

When a transaction corresponding to the requestor's request is not desired, the producer may make block data without a signature for verifying the approval of the transaction. The requestor may view the electronic contract that does not include the signature and may check that the contract fails.

Figure 11:
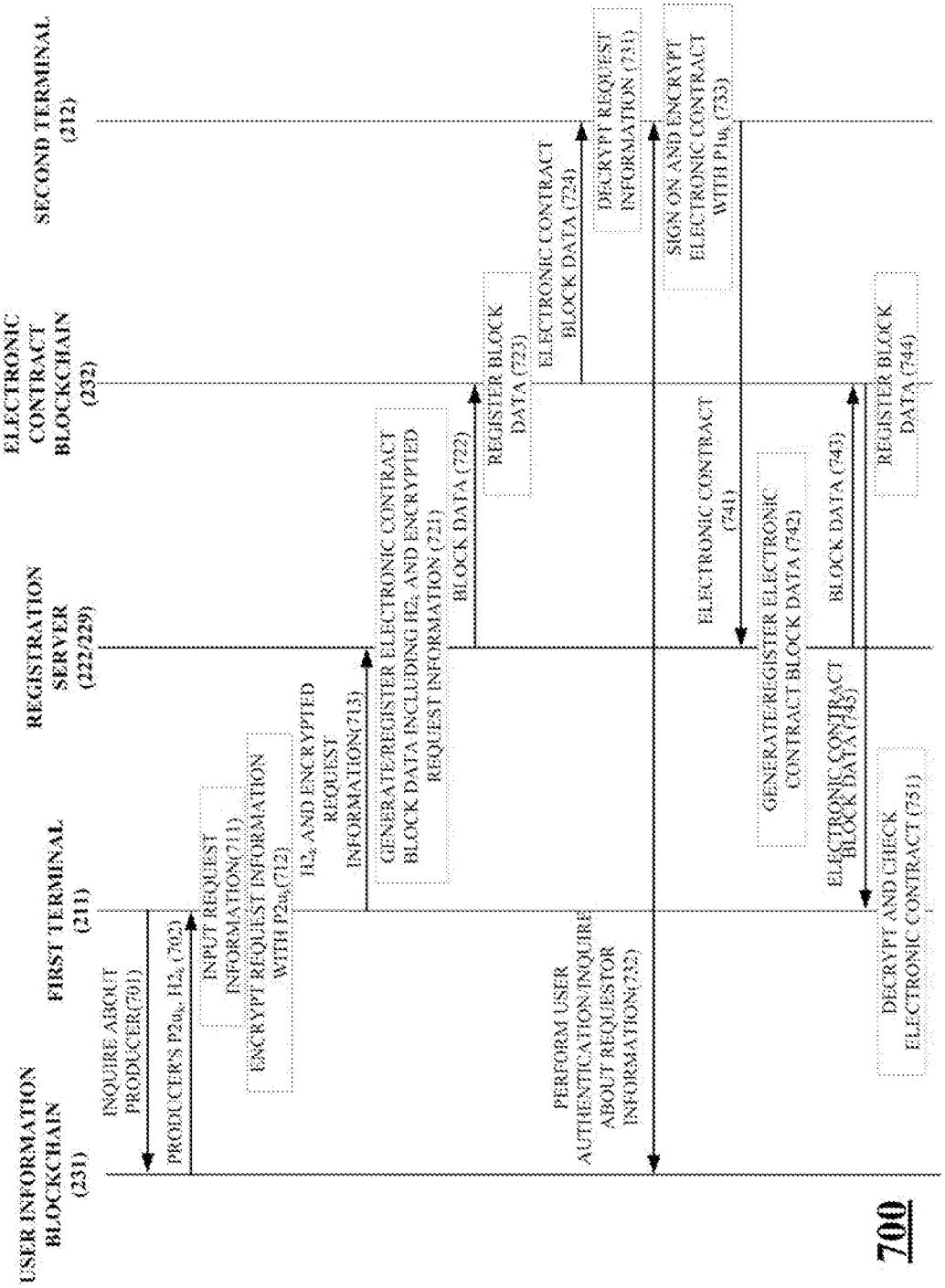
FIG. 11 illustrates another example process of establishing a bio-information data contract.

FIG. 11 illustrates another example process 700 of establishing a bio-information data contract. FIG. 11 illustrates an example operation of the system 200 of FIG. 4 or 5. FIG. 11 is an example contract for a bio-information data generation request between a requestor and a producer. Among user terminals in FIG. 11, a terminal 211 corresponding to the requestor is represented as a first terminal 211, and a terminal 212 corresponding to the producer is represented as a second terminal 212. It is assumed that the first terminal 211 and the second terminal 212 pre-registered their user information.

The first terminal 211 performs user authentication using the user information blockchain 231. When the authentication is successful, the first terminal 211 inquires of the user information blockchain 231 about the producer on the basis of information (user information) regarding the producer (701). The first terminal 211 receives the producer's public key $P2u_k$ and hash key $H2_k$ from the user information blockchain 231 (702).

The first terminal 211 inputs request information (711). The request information refers to all information for generating bio-information data. For example, the request information may include at least one of genome sample information, genomic data information, library information for base sequencing, an analysis date, an analysis method, an analyzer condition, and requestor information. The first terminal 211 encrypts the request information with the public key $P2u_k$ (712). The first terminal 211 transfers the hash key $H2_k$ and the encrypted request information to the electronic contract registration server 222 (713).

The electronic contract registration server 222 generates electronic contract block data including the hash key $H2_k$ and the encrypted request information (721). The electronic contract registration server 222 registers the generated electronic contract block data (721).

The electronic contract registration server 222 delivers the generated electronic contract block data to the electronic contract blockchain 232 (722). The electronic contract blockchain 232 registers the electronic contract block data including the encrypted request information and the hash key $H2_k$ (723).

Subsequently, it may be checked whether the request information is forged or tampered. The user or another entity (a server in the system or an external server for forgery and tampering check) may check whether the request information is changed by comparing corresponding block data registered in the electronic contract registration server 222 to the reference block data stored in the electronic contract blockchain 232.

The electronic contract blockchain 232 transfers the electronic contract block data including the request information to the second terminal 212 on the basis of the hash key $H2_k$ (724). The second terminal 212 decrypts the request information included in the block data with its own encryption key (731). The second terminal 212 may perform user authentication through the user information blockchain 231 (732). When the authentication is successful, the second terminal 212 may inquire of the user information blockchain 231 about the requestor's public key $P1u_k$ and hash key $H1_k$ and may receive the public key $P1u_k$ and the hash key $H1_k$ from the user information blockchain 231 (732). Meanwhile, the request information may pre-include the public key $P1u_k$ and the hash key $H1_k$ of the requestor. Even for the latter case, the second terminal 212 may proceed to a signing step only when the authentication is successful.

The producer checks the request information decrypted with an encryption key that may be symmetric to the requestor's public key and signs on the electronic contract (733). The signature corresponds to verification of user authentication information and transaction approval for the producer. The second terminal 212 may generate a block including the request information, the signature, and the hash key. The second terminal 212 may encrypt (i) the request information or (ii) the request information and the signature with the requestor's public key $P1u_k$ (733). The final electronic contract may include the requestor's hash key $H1_k$, the producer's hash key $H2_k$, the request information encrypted with the requestor's public key $P1u_k$, and the producer's signature key. The producer transmits the electronic contract including the signature and generates bio-information data.

The second terminal 212 transfers the generated electronic contract to the electronic contract registration server 222 (741). The electronic contract registration server 222 generates electronic contract block data including the requestor's hash key $H1_k$, the producer's hash key $H2_k$, the request information encrypted with the requestor's public key $P1u_k$, and the producer's signature key (742). The electronic contract registration server 222 registers the generated electronic contract block data (742). The electronic contract registration server 222 delivers the generated electronic contract block data to the electronic contract blockchain 232 (743). The electronic contract blockchain 232 registers the electronic contract block data (744).

Subsequently, it may be checked whether the electronic contract is forged or tampered. The user or another entity (a server in the system or an external server for forgery and tampering check) may check whether the electronic contract is changed by comparing corresponding block data registered in the electronic contract registration server 222 to the reference block data stored in the electronic contract blockchain 232.

The electronic contract blockchain 232 may deliver the electronic contract to the first terminal 211 on the basis of the requestor's hash key $H1_k$ (745). The first terminal 211 may decrypt the request information/signature included in the received electronic contract with its own encryption key and may check the details of the contract and the approval (751).

When a transaction corresponding to the requestor's request is not desired, the producer may make block data without putting a signature for verifying the approval of the transaction. The requestor may view the electronic contract that does not include the signature and may check that the contract fails.

Figure 12:
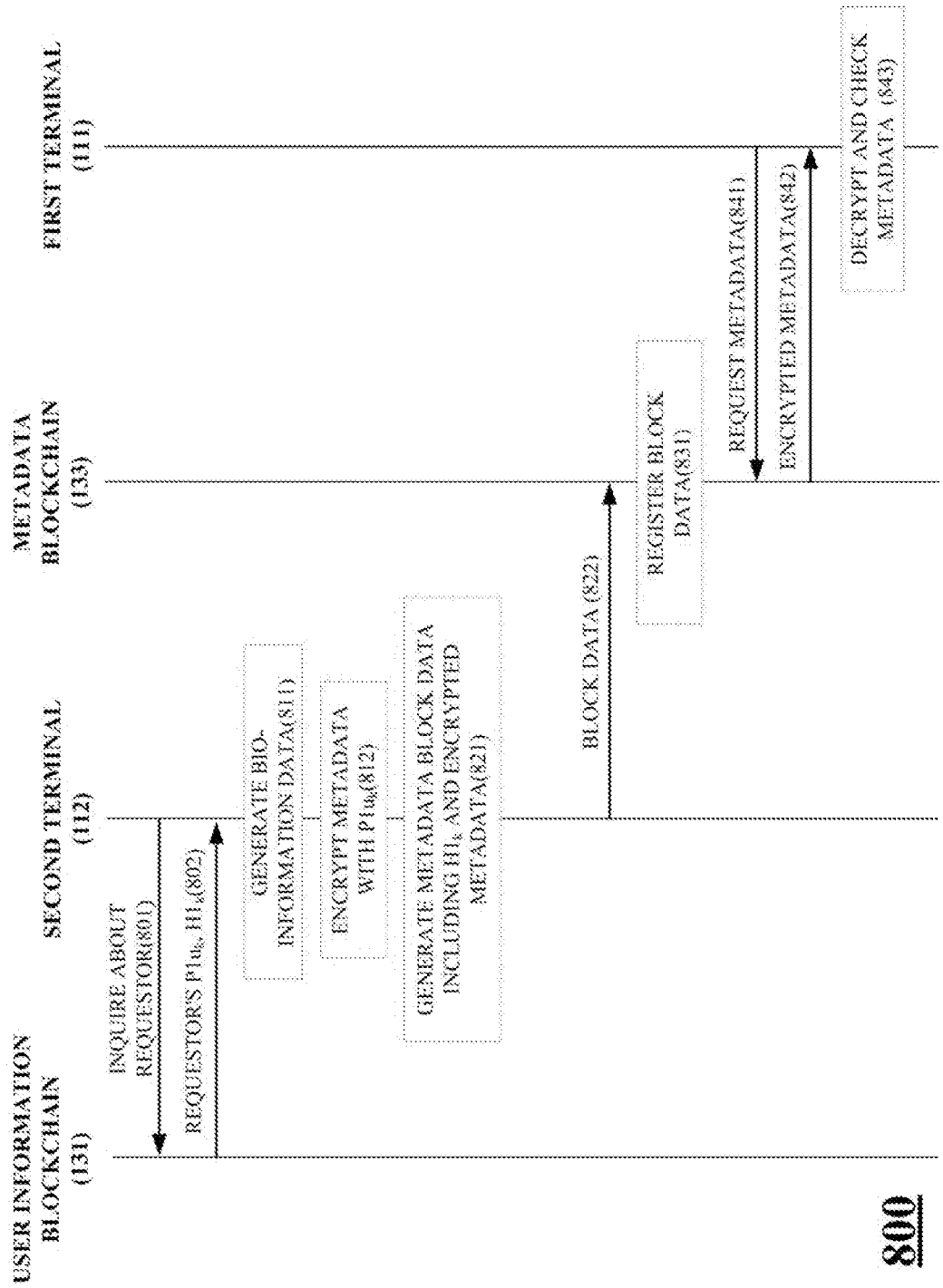
FIG. 12 illustrates an example process of generating metadata.

FIG. 12 illustrates an example process of generating metadata. FIG. 12 illustrates an example operation of the system 100 of FIG. 3. Among user terminals in FIG. 12, a terminal 111 corresponding to the requestor is represented as a first terminal 111, and a terminal 112 corresponding to the producer is represented as a second terminal 112. It is assumed that the first terminal 111 and the second terminal 112 pre-registered their user information.

The second terminal 112 performs user authentication using the user information blockchain 131. When the authentication is successful, the second terminal 112 inquires of the user information blockchain 131 about the requestor on the basis of information (user information) regarding the requestor (801). The second terminal 112 receives the requestor's public key $P1u_k$ and hash key $H1_k$ from the user information blockchain 131 (802).

The second terminal 112 generates bio-information data (811). The second terminal 112 encrypts the bio-information data with the requestor's public key $P1u_k$ (812). The second terminal 112 generates metadata block data including the hash key $H1_k$ and the encrypted bio-information data (821). The second terminal 112 delivers the generated metadata block data to the metadata blockchain 133 (822). The metadata blockchain 133 registers the received metadata block data to configure a blockchain (831).

The metadata may be automatically transferred to the first terminal 111. Alternatively, when the first terminal 111 requests the metadata on the basis of its own hash key or the like (841), the first terminal 111 may receive the encrypted metadata from the metadata blockchain 133 (842). The first terminal 111 may decrypt the metadata with its own encryption key and check the metadata (843).

Figure 13:
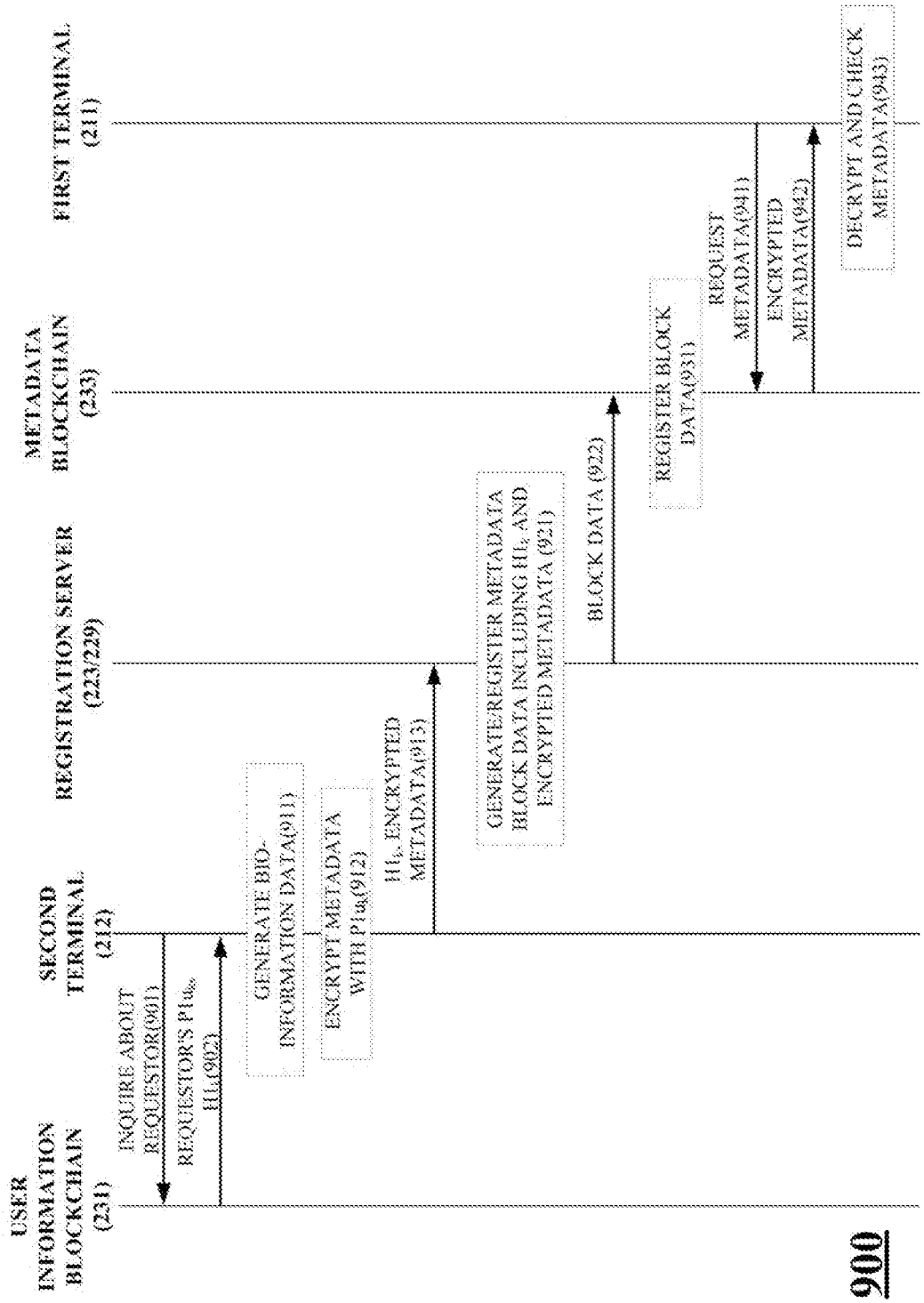
FIG. 13 illustrates another example process of generating metadata.

FIG. 13 illustrates another example process of generating metadata. FIG. 13 illustrates an example operation of the system 200 of FIG. 4 or 5. Among user terminals in FIG. 13, a terminal 211 corresponding to the requestor is represented as a first terminal 211, and a terminal 212 corresponding to the producer is represented as a second terminal 212. It is assumed that the first terminal 211 and the second terminal 212 pre-registered their user information.

The second terminal 212 performs user authentication using the user information blockchain 231. When the authentication is successful, the second terminal 212 inquires of the user information blockchain 231 about the requestor on the basis of information (user information) regarding the requestor (901). The second terminal 212 receives the requestor's public key $P1u_k$ and hash key $H1_k$ from the user information blockchain 231 (902).

The second terminal 212 generates bio-information data (911). The second terminal 212 encrypts the bio-information data with the requestor's public key $P1u_k$ (912). The second terminal 212 transfers the hash key $H1_k$ and the encrypted bio-information data to the metadata registration server 223 (913). The metadata registration server 223 generates metadata block data including the hash key $H1_k$ and the encrypted bio-information data (921). The metadata registration server 223 registers the generated metadata block data (921). The metadata registration server 223 delivers the generated metadata bock data to the metadata blockchain 233 (922). The metadata blockchain 233 registers the received metadata block data to configure a blockchain (931).

Subsequently, it may be checked whether the metadata is forged or tampered. The user or another entity (a server in the system or an external server for forgery and tampering check) may check whether the metadata is changed by comparing corresponding block data registered in the metadata registration server 223 to the reference block data stored in the metadata blockchain 233.

The metadata may be automatically transferred to the first terminal 211. Alternatively, when the first terminal 211 requests the metadata on the basis of its own hash key or the like (941), the first terminal 211 may receive the encrypted metadata from the metadata blockchain 233 (942). The first terminal 211 may decrypt the metadata with its own encryption key and check the metadata (943).

Figure 14:
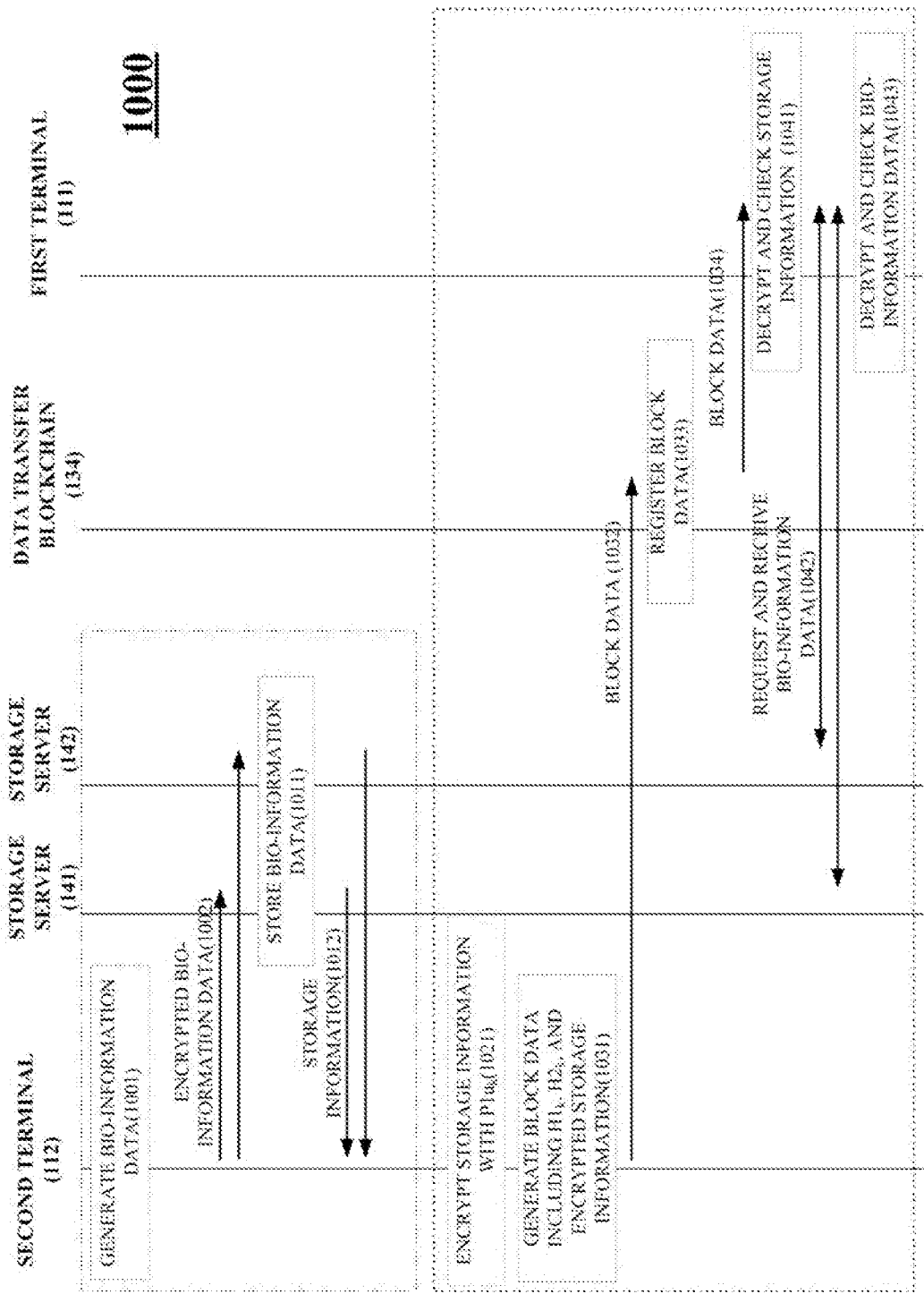
FIG. 14 illustrates an example process of delivering bio-information data.

FIG. 14 illustrates an example process of delivering bio-information data. FIG. 14 illustrates an example operation of a system similar to the system 100 of FIG. 3. FIG. 14 is an example of not using the data storage blockchain but using a typical storage server for simply storing data. Among user terminals in FIG. 14, a terminal 111 corresponding to the requestor is represented as a first terminal 111, and a terminal 112 corresponding to the producer is represented as a second terminal 112. It is assumed that the first terminal 111 and the second terminal 112 pre-registered their user information. The process of FIG. 14 assumes that the first terminal 111 and the second terminal 112 performed user authentication through the user information blockchain 131 and received information (public keys and hash keys) regarding their counter terminals.

The second terminal 112 generates bio-information data (1001). The second terminal 112 knows the requestor's public key $P1u_k$ and hash key $H1_k$. The second terminal 112 encrypts the bio-information data with the requestor's public key $P1u_k$ and transfers the encrypted bio-information data to the storage servers 141 and 142 (1002). The second terminal 112 may store the encrypted bio-information data in a single storage server 141 or 142 (1011). Alternatively, the second terminal 112 may store the encrypted bio-information data in a plurality of storage servers 141, 142, and so on in a distributed manner (1011). The storage servers 141 and 142 notify the second terminal 112 of storage information after storing the bio-information data (1012). The storage information may include at least one of the storage servers' identifiers, locations where the bio-information data is stored in storage media of the storage servers, verification keys, file sizes, and file partitioning information. In FIG. 14, the operations 1001 to 1012 correspond to a bio-information data storage step.

The second terminal 112 encrypts the storage information with the requestor's public key $P1u_k$ (1021). The second terminal 112 may generate transfer block data including the requestor's hash key $H1_k$ and the encrypted storage information (1031). Alternatively, the second terminal 112 may generate transfer block data including the requestor's hash key $H1_k$, the producer's hash key $H2_k$, and the encrypted storage information (1031).

The second terminal 112 transfers the generated transfer block data to the data transfer blockchain 134 (1032). The data transfer blockchain 134 registers the transfer block data to configure a blockchain (1033).

Subsequently, it may be checked whether the storage information is forged or tampered. The user or another entity (a server in the system or an external server for forgery and tampering check) may check whether the storage information is changed by comparing corresponding block data registered in the data transfer registration server 124 to the reference block data stored in the data transfer blockchain 134.

The data transfer blockchain 134 may transfer the encrypted storage information to the first terminal 111 on the basis of the requestor's hash key $H1_k$ (1034). The first terminal 111 decrypts the encrypted storage information with its own encryption key and checks the storage information (1041). Depending on the storage information, the first terminal 111 may request bio-information data from the storage server 141 or 142 in which the bio-information data is stored and may receive the bio-information data from the corresponding storage server (1042). In this case, the received bio-information data is encrypted. The first terminal 111 may decrypt the bio-information data with its own encryption key and check the bio-information data (1043).

Figure 15:
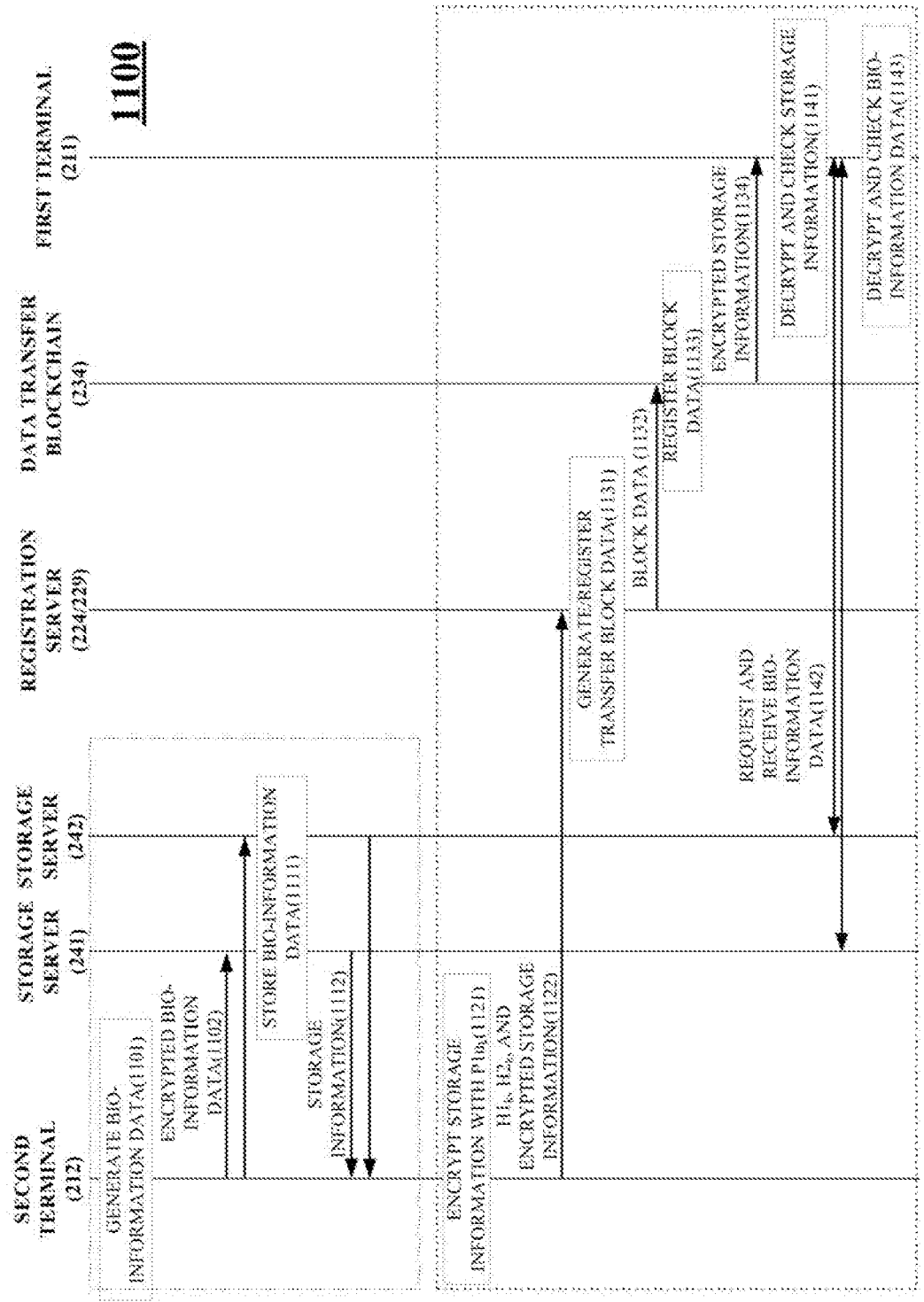
FIG. 15 illustrates another example process of delivering bio-information data.

FIG. 15 illustrates another example process of delivering bio-information data. FIG. 15 illustrates an example operation of a system similar to the system 200 of FIG. 6. FIG. 15 is an example of not using the data storage blockchain but using a typical storage server for simply storing data. Among user terminals in FIG. 15, a terminal 211 corresponding to the requestor is represented as a first terminal 211, and a terminal 212 corresponding to the producer is represented as a second terminal 212. It is assumed that the first terminal 211 and the second terminal 212 pre-registered their user information. The process of FIG. 15 assumes that the first terminal 211 and the second terminal 212 performed user authentication through the user information blockchain 231 and received information (public keys and hash keys) regarding their counter terminals.

The second terminal 212 generates bio-information data (1101). The second terminal 212 knows the requestor's public key $P1u_k$ and hash key $H1_k$. The second terminal 212 encrypts the bio-information data with the requestor's public key $P1u_k$ and transfers the encrypted bio-information data to the storage servers 241 and 242 (1102). The second terminal 212 may store the encrypted bio-information data in a single storage server 241 or 242 (1111). Alternatively, the second terminal 212 may store the encrypted bio-information data in a plurality of storage servers 241, 242, and so on in a distributed manner (1111). The storage servers 241 and 242 notify the second terminal 212 of storage information after storing the bio-information data (1112). The storage information may include at least one of the storage servers' identifiers, locations where the bio-information data is stored in storage media of the storage servers, verification keys, file sizes, and file partitioning information. In FIG. 15, the operations 1101 to 1112 correspond to a bio-information data storage step.

The second terminal 212 encrypts the storage information with the requestor's public key $P1u_k$ (1121). The second terminal 212 may transfer the requestor's hash key $H1_k$ and the encrypted storage information to the data transfer registration server 224 (1122). Alternatively, the second terminal 212 may transfer the requestor's hash key $H1_k$, the producer's hash key $H2_k$, and the encrypted storage information to the data transfer registration server 224 (1122).

The data transfer registration server 224 generates transfer block data including the received hash key and the encrypted storage information (1131). The data transfer registration server 224 registers the generated transfer block data (1131).

The data transfer registration server 224 transfers the generated transfer block data to the data transfer blockchain 234 (1132). The data transfer blockchain 234 registers the transfer block data to configure a blockchain (1133).

Subsequently, it may be checked whether the storage information is forged or tampered. The user or another entity (a server in the system or an external server for forgery and tampering check) may check whether the storage information is changed by comparing corresponding block data registered in the data transfer registration server 224 to the reference block data stored in the data transfer blockchain 234.

The data transfer blockchain 234 may transfer the encrypted storage information to the first terminal 211 on the basis of the requestor's hash key $H1_k$ (1134). The first terminal 211 decrypts the encrypted storage information with its own encryption key and checks the storage information (1141). Depending on the storage information, the first terminal 211 may request bio-information data from the storage server 241 or 242 in which the bio-information data is stored and may receive the bio-information data from the corresponding storage server (1142). In this case, the received bio-information data is encrypted. The first terminal 211 may decrypt the bio-information data with its own encryption key and check the metadata (1143).

Figure 16:
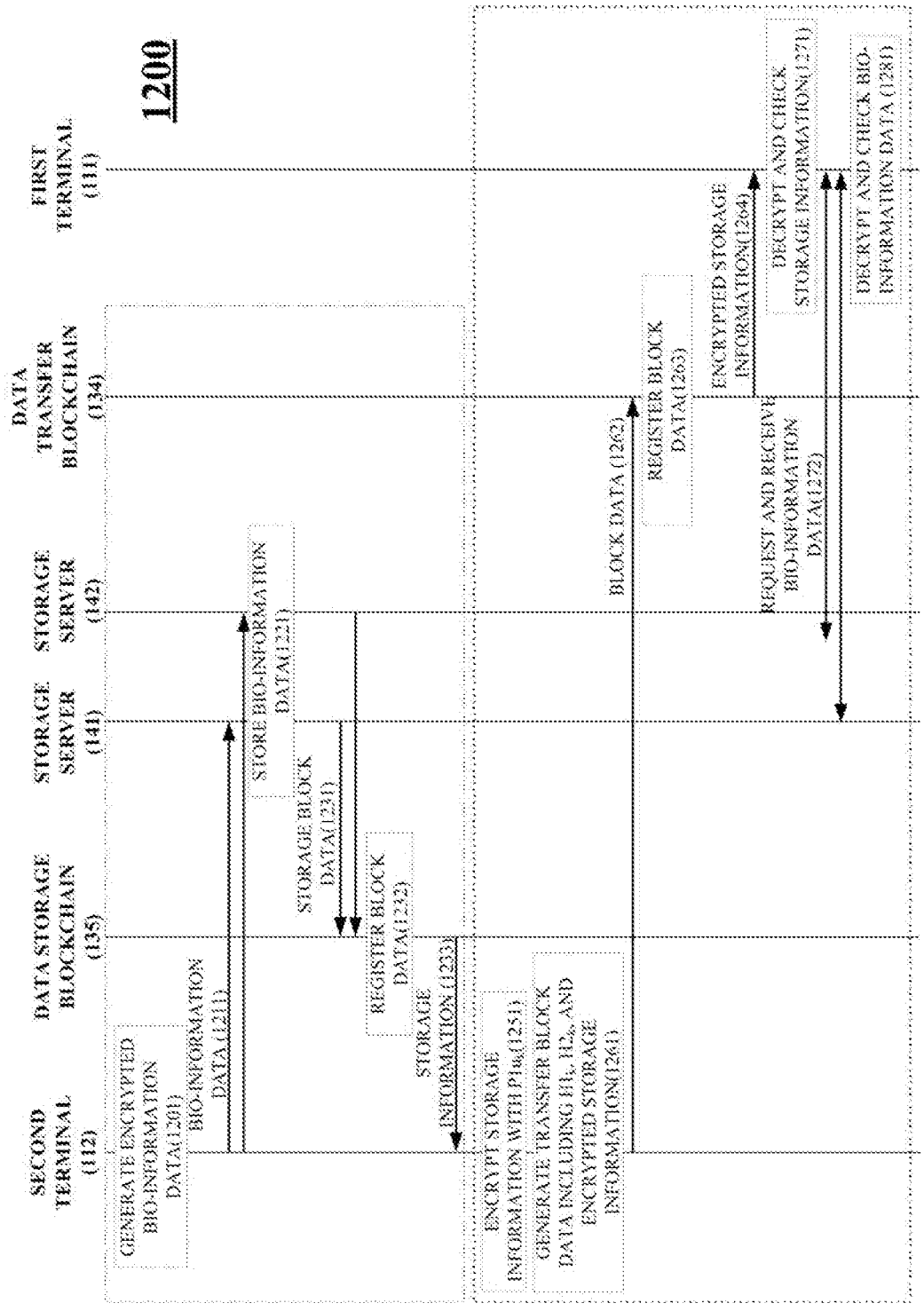
FIG. 16 illustrates still another example process of delivering bio-information data.

FIG. 16 illustrates still another example process of transferring bio-information data. FIG. 16 illustrates an example operation of the system 100 of FIG. 3. Among user terminals in FIG. 16, a terminal 111 corresponding to the requestor is represented as a first terminal 111, and a terminal 112 corresponding to the producer is represented as a second terminal 112. It is assumed that the first terminal 111 and the second terminal 112 pre-registered their user information.

FIG. 16 indicates a case in which a plurality of storage servers hold bio-information data in the form of a blockchain.

The second terminal 112 generates bio-information data (1201). The second terminal 112 knows the requestor's public key $P1u_k$ and hash key $H1_k$. The second terminal 112 encrypts the bio-information data with the requestor's public key $P1u_k$ and transfers the encrypted bio-information data to the storage servers 141 and 142 (1211). In this case, the second terminal 112 may transfer its own hash key $H2_k$ to the storage servers 141 and 142.

The storage servers 141 and 142 store the hash key $H2_k$ and the encrypted bio-information data (1222). The plurality of storage servers 141 and 142 may store the bio-information data in a distributed manner. Among the plurality of storage servers, one server (a main storage server) may store the generated bio-information data itself, and the other servers (sub-storage servers) may store the bio-information data in a distributed (divided) manner. The plurality of storage servers or the plurality of sub-storage servers may serve as nodes constituting a blockchain such that the plurality of storage servers constitute a data storage blockchain.

The storage servers 141 and 142 deliver storage information to the data storage blockchain 135 in the form of a block (1231). The data storage blockchain 135 registers the storage block data to configure a blockchain (1232). The storage servers 141 and 142 may serve as nodes constituting the data storage blockchain 135. Alternatively, the data storage blockchain 135 may be configured using a separate server.

The data storage blockchain 135 delivers block data including the storage information to the second terminal 112 on the basis of the hash key $H2_k$ (1233). The storage information may include at least one of the storage servers' identifiers, locations where the bio-information data is stored in storage media of the storage servers, verification keys, file sizes, and file partitioning information. In FIG. 16, the operations 1201 to 1233 correspond to a bio-information data storage step.

The second terminal 112 encrypts the storage information with the requestor's public key $P1u_k$ (1251). The second terminal 112 may generate transfer block data including the requestor's hash key $H1_k$ and the encrypted storage information (1261). Alternatively, the second terminal 112 may generate transfer block data including the requestor's hash key $H1_k$, the producer's hash key $H2_k$, and the encrypted storage information (1261). The second terminal 112 transfers the generated transfer block data to the data transfer blockchain 134 (1262). The data transfer blockchain 134 registers the transfer block data to configure a blockchain (1263).

The data transfer blockchain 134 may transfer the encrypted storage information to the first terminal 111 on the basis of the requestor's hash key $H1_k$ (1264). The first terminal 111 decrypts the encrypted storage information with its own encryption key and checks the storage information (1271). Depending on the storage information, the first terminal 111 may request bio-information data from the storage server 141 or 142 in which the bio-information data is stored and may receive the bio-information data from the corresponding storage server (1272). In this case, the received bio-information data is encrypted. The first terminal 111 may decrypt the bio-information data with its own encryption key and check the bio-information data (1281).

Figure 17:
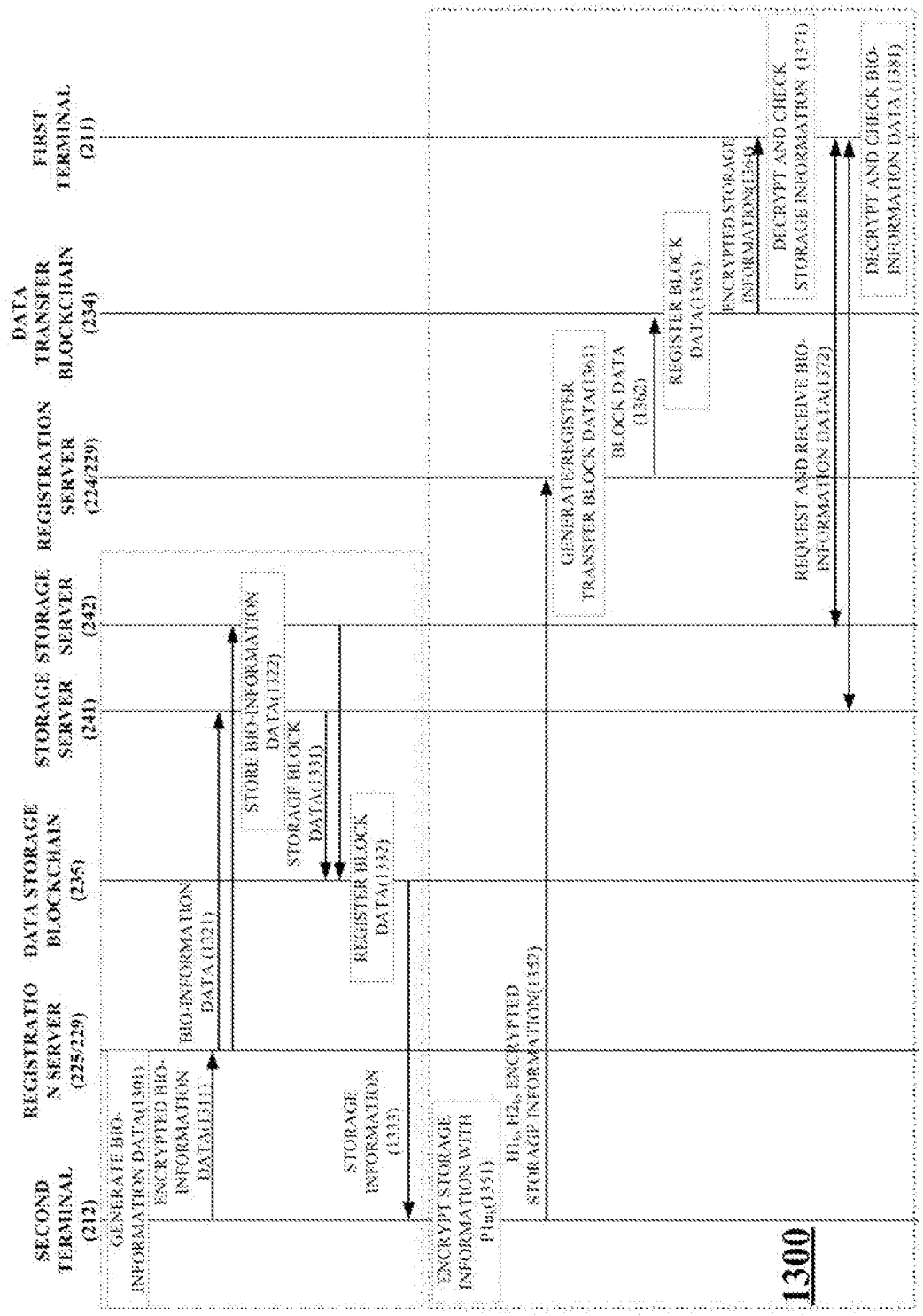
FIG. 17 illustrates still another example process of delivering bio-information data.

FIG. 17 illustrates still another example process of transferring bio-information data. FIG. 17 illustrates an example operation of the system 200 of FIG. 4 or 5. Among user terminals in FIG. 17, a terminal 211 corresponding to the requestor is represented as a first terminal 211, and a terminal 212 corresponding to the producer is represented as a second terminal 212. It is assumed that the first terminal 211 and the second terminal 212 pre-registered their user information. FIG. 17 indicates a case in which a plurality of storage servers hold bio-information data in the form of a blockchain.

The second terminal 212 generates bio-information data (1301). The second terminal 212 knows the requestor's public key $P1u_k$ and hash key $H1_k$. The second terminal 212 encrypts the bio-information data with the requestor's public key $P1u_k$ and transfers the encrypted bio-information data to an information storage registration server 225 (1311). In this case, the second terminal 212 may transfer its own hash key $H2_k$ to the information storage registration server 225. The information storage registration server 225 delivers the hash key $H2_k$ and the bio-information data to the storage servers 241 and 242 (1321). The plurality of storage servers 241 and 242 may store the bio-information data in a distributed manner (1322). Among the plurality of storage servers, one server (a main storage server) may store the generated bio-information data itself, and the other servers (sub-storage servers) may store the bio-information data in a distributed (divided) manner. The plurality of storage servers or the plurality of sub-storage servers may serve as nodes constituting a blockchain such that the plurality of storage servers constitute a data storage blockchain.

The storage servers 241 and 242 deliver storage information to the data storage blockchain 235 in the form of a block (1331). The data storage blockchain 235 registers the storage block data to configure a blockchain (1332). The storage servers 241 and 242 may serve as nodes constituting the data storage blockchain 235. Alternatively, the data storage blockchain 235 may be configured using a separate server. The data storage blockchain 235 delivers block data including the storage information to the second terminal 212 on the basis of the hash key $H2_k$ (1333). The storage information may include at least one of the storage servers' identifiers, locations where the bio-information data is stored in storage media of the storage servers, verification keys, file sizes, and file partitioning information. In FIG. 17, the operations 1301 to 1333 correspond to a bio-information data storage step.

The second terminal 212 encrypts the storage information with the requestor's public key $P1u_k$ (1351). The second terminal 212 transfers the requestor's hash key $H1_k$ and the encrypted storage information to the data transfer registration server 224 (1352). Alternatively, the second terminal 212 may transfer the requestor's hash key $H1_k$, the producer's hash key $H2_k$, and the encrypted storage information to the data transfer registration server 224 (1352).

The data transfer registration server 224 generates transfer block data including the received hash key and the encrypted storage information (1361). The data transfer registration server 224 registers the generated transfer block data (1361).

The data transfer registration server 224 transfers the generated transfer block data to the data transfer blockchain 234 (1362). The data transfer blockchain 234 registers the transfer block data to configure a blockchain (1363).

Subsequently, it may be checked whether the storage information is forged or tampered. The user or another entity (a server in the system or an external server for forgery and tampering check) may check whether the storage information is changed by comparing corresponding block data registered in the data transfer registration server 224 to the reference block data stored in the data transfer blockchain 234.

The data transfer blockchain 234 may transfer the encrypted storage information to the first terminal 211 on the basis of the requestor's hash key $H1_k$ (1364). The first terminal 211 decrypts the encrypted storage information with its own encryption key and checks the storage information (1371). Depending on the storage information, the first terminal 211 may request bio-information data from the storage server 241 or 242 in which the bio-information data is stored and may receive the bio-information data from the corresponding storage server (1372). In this case, the received bio-information data is encrypted. The first terminal 211 may decrypt the bio-information data with its own encryption key and check the bio-information data (1381).

Figure 18:
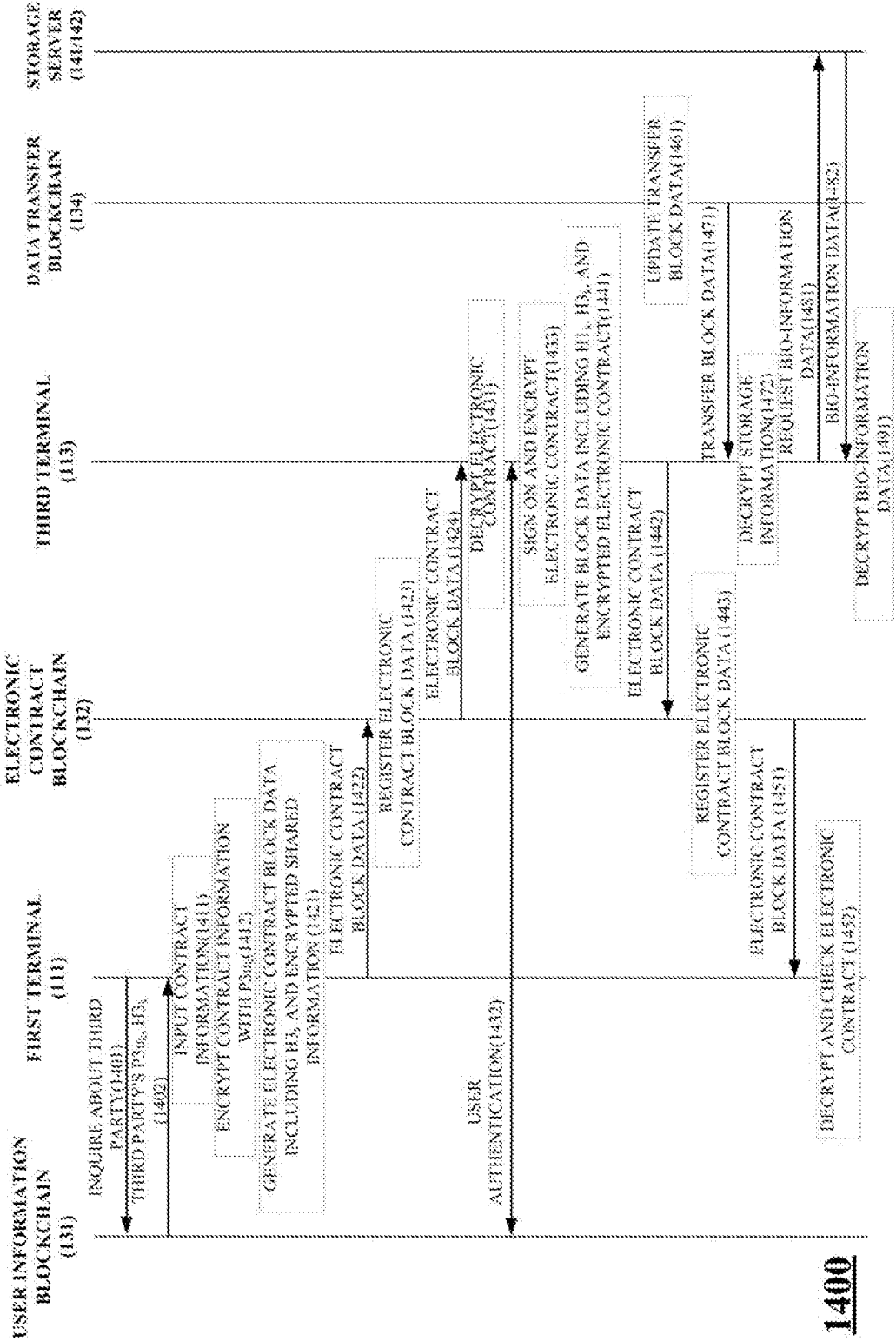
FIG. 18 illustrates an example process of sharing bio-information data with a third party.

FIG. 18 illustrates an example process of sharing bio-information data with a third party. FIG. 18 illustrates an example operation of the system 100 of FIG. 3. FIG. 18 shows an example process in which the requestor shares bio-information data provided by the producer with a third party. Among user terminals in FIG. 18, a terminal 111 corresponding to the requestor is represented as a first terminal 111, and a terminal 113 corresponding to the third party is represented as a third terminal 113. It is assumed that the first terminal 111 and the third terminal 113 pre-registered their user information.

The first terminal 111 performs user authentication using the user information blockchain 131. When the authentication is successful, the first terminal 111 inquires of the user information blockchain 131 about the third party on the basis of information (user information) regarding the producer (1401). The first terminal 111 receives the third party's public key $P3u_k$ and hash key $H3_k$ from the user information blockchain 131 (1402).

The first terminal 111 inputs contract information (1411). The contract information corresponds to information regarding a contract between the requestor and the third party. The contract information includes a new contract term. For example, the contract information may include information for sharing the bio-information data with the third party. In this case, the contract information may include at least one of the above-described storage information, a sharing period, a sharing condition, genome sample information, bio-information data, library information for base sequencing, an analysis date, an analysis method, an analyzer condition, producer information, and requestor information. The first terminal 111 encrypts the shared information with the public key $P3u_k$ (1412). The first terminal 111 generates electronic contract block data including the hash key $H3_k$ and the encrypted contract information (1421). The first terminal 111 delivers the generated electronic contract block data to the electronic contract blockchain 132 (1422). The electronic contract blockchain 132 registers the electronic contract block data including the encrypted shared information and the hash key $H2_k$ (1423).

The electronic contract blockchain 132 transfers the electronic contract block data including the contract information to the third terminal 113 on the basis of the hash key $H3_k$ (1424). The third terminal 113 decrypts the shared information included in the block data with its own encryption key (1431). The third terminal 113 may perform user authentication through the user information blockchain 131 (1432). When the authentication is successful, the third terminal 113 may inquire of the user information blockchain 131 about the requestor's public key $P1u_k$ and hash key $H1_k$ and may receive the public key $P1u_k$ and the hash key $H1_k$ from the user information blockchain 131 (1432). Meanwhile, the shared information may pre-include the requestor's public key $P1u_k$ and hash key $H1_k$. Even for the latter case, the third terminal 113 may proceed to a signing step only when the authentication is successful.

The third party checks the shared information decrypted with its own encryption key and signs on the electronic contract (1433). The signature corresponds to verification of user authentication information and transaction approval. The third terminal 113 may generate a block including the contract information, the signature, and the hash key. The third terminal 113 may encrypt (i) the contract information or (ii) the contract information and the signature with the requestor's public key $P1u_k$ (1433). The final electronic contract may include the requestor's hash key $H1_k$, the third party's hash key $H3_k$, the contract information encrypted with the requestor's public key $P1u_k$, and the third party's signature key.

The third terminal 113 generates electronic contract block data including the requestor's hash key $H1_k$, the third party's hash key $H3_k$, the contract information encrypted with the requestor's public key $P1u_k$, and the third party's signature key (1441). The third terminal 113 delivers the generated electronic contract block data to the electronic contract blockchain 132 (1442). The electronic contract blockchain 132 registers the electronic contract block data (1443).

The electronic contract blockchain 132 may deliver the electronic contract to the first terminal 111 on the basis of the requestor's hash key $H1_k$ (1451). The first terminal 111 may decrypt the contract information/signature included in the received electronic contract with its own encryption key and may check the details of the contract and the approval (1452).

Although not specifically shown in FIG. 18, the transfer block data stored in the data transfer blockchain 134 may be updated (1461). Specifically, the first terminal 111 may deliver the transfer block data including the storage information encrypted with the third party's public key $P3u_k$ to the data transfer blockchain 234 and store the delivered transfer block data in the data transfer blockchain 234. Also, the first terminal 111 may encrypt the bio-information data with the third party's public key $P3u_k$ and may pre-store the encrypted bio-information data in the data storage blockchain 135 through a plurality of storage servers.

Subsequently, the third terminal 113 receives the transfer block data from the data transfer blockchain 134 on the basis of the requestor's hash key $H1_k$ (1471). The storage information may be encrypted. The third terminal 113 decrypts the storage information with its own encryption key (1472). Depending on the decrypted storage information, the third terminal 113 requests the bio-information data from the storage server 141 or 142 (1481) and receives the bio-information data (1482). The third terminal 113 may decrypt the bio-information data with its own encryption key (1491).

The requestor fundamentally has priority in a bio-information data production contract. Thus, FIG. 18 shows an entity who shares bio-information data as the requestor. However, the producer may share the bio-information data with a third party under pre-contracted terms. In this case, as shown in FIG. 18, the second terminal 112 may perform the operation of the first terminal 111.

Figure 19:
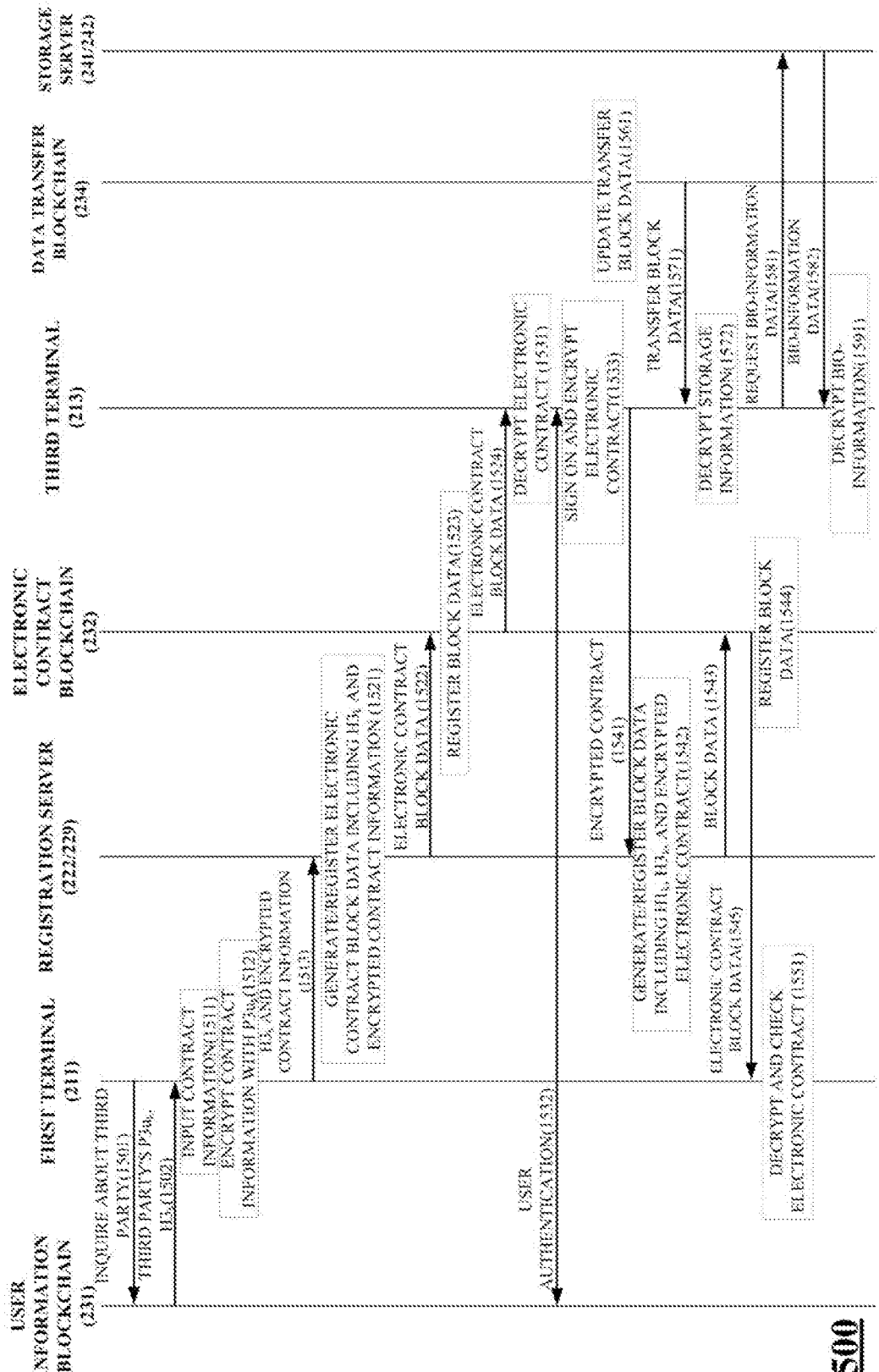
FIG. 19 illustrates another example process of sharing bio-information data with a third party.

FIG. 19 illustrates another example process of sharing bio-information data with a third party. FIG. 19 illustrates an example operation of the system 200 of FIG. 4 or 5. FIG. 19 shows an example process in which the requestor shares bio-information data provided by the producer with a third party. Among user terminals in FIG. 19, a terminal 211 corresponding to the requestor is represented as a first terminal 211, and a terminal 213 corresponding to the third party is represented as a third terminal 213. It is assumed that the first terminal 211 and the third terminal 213 pre-registered their user information.

The first terminal 211 performs user authentication using the user information blockchain 231. When the authentication is successful, the first terminal 211 inquires of the user information blockchain 231 about the third party on the basis of information (user information) regarding the producer (1501). The first terminal 211 receives the third party's public key $P3u_k$ and hash key $H3_k$ from the user information blockchain 231 (1502).

The first terminal 211 inputs contract information (1511). The contract information corresponds to information regarding a contract between the requestor and the third party. The contract information corresponds to information regarding a contract between the requestor and the third party. The contract information includes a new contract term. For example, the contract information may include information for sharing the bio-information data with the third party. In this case, the contract information may include at least one of the above-described storage information, a sharing period, a sharing condition, genome sample information, genomic data information, library information for base sequencing, an analysis date, an analysis method, an analyzer condition, producer information, and requestor information. The first terminal 211 encrypts the contract information with the public key $P3u_k$ (1521). The first terminal 211 transfers the hash key $H3_k$ and the encrypted request information to the electronic contract registration server 222 (1513).

The electronic contract registration server 222 generates electronic contract block data including the hash key $H3_k$ and the encrypted contract information (1521). The electronic contract registration server 222 registers the generated electronic contract block data (1521).

The electronic contract registration server 222 delivers the generated electronic contract block data to the electronic contract blockchain 232 (1522). The electronic contract blockchain 232 registers the electronic contract block data including the encrypted contract information and the hash key $H2_k$ (1523).

Subsequently, it may be checked whether the contract information is forged or tampered. The user or another entity (a server in the system or an external server for forgery and tampering check) may check whether the contract information is changed by comparing corresponding block data registered in the electronic contract registration server 222 to the reference block data stored in the electronic contract blockchain 232.

The electronic contract blockchain 232 transfers the electronic contract block data including the contract information to the third terminal 213 on the basis of the hash key $H3_k$ (1524). The third terminal 213 decrypts the contract information included in the block data with its own encryption key (1531). The third terminal 213 may perform user authentication through the user information blockchain 231 (1532). When the authentication is successful, the third terminal 213 may inquire of the user information blockchain 231 about the requestor's public key $P1u_k$ and hash key $H1_k$ and may receive the public key $P1u_k$ and the hash key $H1_k$ from the user information blockchain 231 (1532). Meanwhile, the contract information may pre-include the requestor's public key $P1u_k$ and hash key $H1_k$. Even for the latter case, the third terminal 213 may proceed to a signing step only when the authentication is successful.

The producer checks the contract information decrypted with its own encryption key and signs on the electronic contract (1533). The signature corresponds to verification of user authentication information and transaction approval for the producer. The third terminal 213 may generate a block including the contract information, the signature, and the hash key. The third terminal 213 may encrypt (i) the contract information or (ii) the contract information and the signature with the requestor's public key $P1u_k$ (1533). The final electronic contract may include the requestor's hash key $H1_k$, the third party's hash key $H3_k$, the contract information encrypted with the requestor's public key $P1u_k$, and the third party's signature key. The third party transmits the electronic contract including the signature and generates bio-information data.

The third terminal 213 transfers the generated electronic contract to the electronic contract registration server 222 (1541). The electronic contract registration server 222 generates electronic contract block data including the requestor's hash key $H1_k$, the third party's hash key $H3_k$, the contract information encrypted with the requestor's public key $P1u_k$, and the third party's signature key (1542). The electronic contract registration server 222 registers the generated electronic contract block data (1542). The electronic contract registration server 222 delivers the generated electronic contract block data to the electronic contract blockchain 232 (1543). The electronic contract blockchain 232 registers the electronic contract block data (1544).

Subsequently, it may be checked whether the electronic contract is forged or tampered. The user or another entity (a server in the system or an external server for forgery and tampering check) may check whether the electronic contract is changed by comparing corresponding block data registered in the electronic contract registration server 222 to the reference block data stored in the electronic contract blockchain 232.

The electronic contract blockchain 232 may deliver the electronic contract to the first terminal 211 on the basis of the requestor's hash key $H1_k$ (1545). The first terminal 211 may decrypt the contract information/signature included in the received electronic contract with its own encryption key and may check the details of the contract and the approval (1551).

Although not specifically shown in FIG. 19, the transfer block data stored in the data transfer blockchain 234 may be updated (1561). Specifically, the first terminal 211 may encrypt the storage information with the third party's public key $P3u_k$ and deliver the encrypted storage information to the data transfer registration server 224. The data transfer registration server 224 may deliver and store the encrypted storage information to and in the data transfer blockchain 234. Alternatively, the first terminal 211 may encrypt the bio-information data with the third party's public key $P3u_k$ and deliver the encrypted bio-information data to the information storage registration server 225. The information storage registration server 225 may pre-store the encrypted bio-information data in a genomic information storage blockchain 235 through a plurality of storage servers.

Subsequently, the third terminal 213 receives the storage information block data (1571) from the data transfer blockchain 234 on the basis of the requestor's hash key $H1_k$. The storage information may be encrypted. The third terminal 213 decrypts the storage information with its own encryption key (1572). Depending on the decrypted storage information, the third terminal 213 requests the bio-information data from the storage server 241 or 242 (1581) and receives the bio-information data (1582). The third terminal 213 may decrypt the bio-information data with its own encryption key (1591).

The requestor fundamentally has priority in a bio-information data production contract. Thus, FIG. 19 shows an entity who shares bio-information data as the requestor. However, the producer may share the bio-information data with a third party under pre-contracted terms. In this case, as shown in FIG. 19, the second terminal 212 may perform the operation of the first terminal 211.

Figure 20:
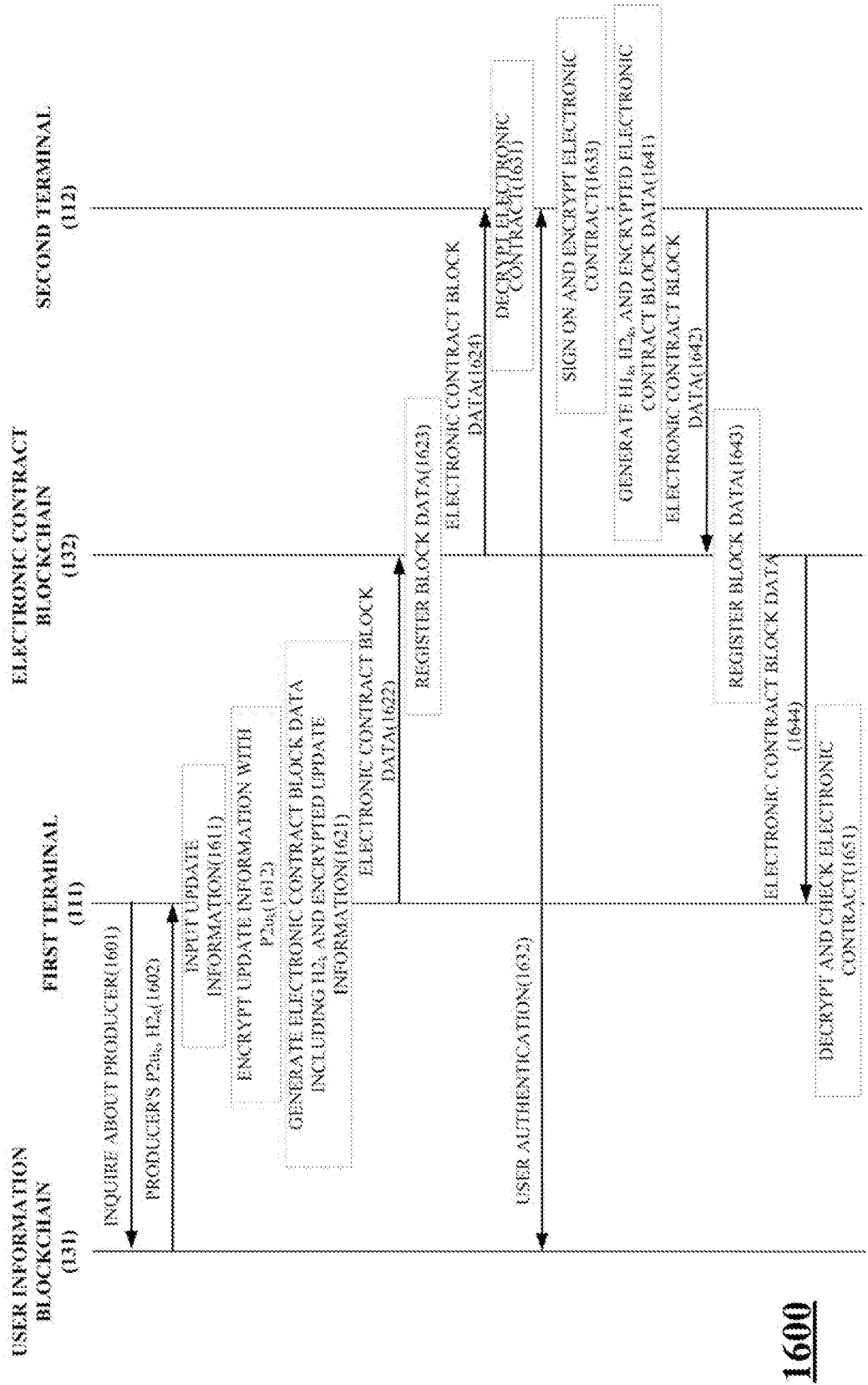
FIG. 20 illustrates an example process of updating a contract.

FIG. 20 illustrates an example process of updating a contract. FIG. 20 illustrates an example operation of the system 100 of FIG. 3. FIG. 20 is an example process of changing and updating information regarding a contract between the requestor and the producer. The following description with reference to FIG. 20 focuses on the client and the producer, but the same process is applied to an update of a contract between the requestor and a third party. Among user terminals in FIG. 20, a terminal 111 corresponding to the requestor is represented as a first terminal 111, and a terminal 112 corresponding to the producer is represented as a second terminal 112. It is assumed that the first terminal 111 and the second terminal 112 pre-registered their user information.

The first terminal 111 performs user authentication using the user information blockchain 131. When the authentication is successful, the first terminal 111 inquires of the user information blockchain 131 about the producer on the basis of information (user information) regarding the producer (1601). The first terminal 111 receives the producer's public key $P2u_k$ and hash key $H2_k$ from the user information blockchain 131 (1602).

The first terminal 111 inputs update information (1611). The update information includes information for changing the details of the contract. For example, the update information may include a change of a contract period, a change of requested details, a change of a contracting entity, a request to release a contract, contract end information, a request to delete bio-information data, a request to delete generated data, and the like. When the update information is a request to delete specific data, the update information may include an identifier of target data, producer information, requestor information, deletion conditions, etc. The first terminal 111 encrypts the update information with the public key $P2u_k$ (1612). The first terminal 111 generates electronic contract block data including the hash key $H2_k$ and the encrypted update information (1621). The first terminal 111 delivers the generated electronic contract block data to the electronic contract blockchain 132 (1622). The electronic contract blockchain 132 registers the electronic contract block data including the encrypted update information and the hash key $H2_k$ (1623).

The electronic contract blockchain 132 transfers the electronic contract block data including the update information to the second terminal 112 on the basis of the hash key $H2_k$ (1624). The second terminal 112 decrypts the update information included in the block data with its own encryption key (1631). The second terminal 112 may perform user authentication through the user information blockchain 131 (1632). When the authentication is successful, the second terminal 112 may inquire of the user information blockchain 131 about the requestor's public key $P1u_k$ and hash key $H1_k$ and may receive the public key $P1u_k$ and the hash key $H1_k$ from the user information blockchain 131. Meanwhile, the update information may pre-include the requestor's public key $P1u_k$ and hash key $H1_k$. Even for the latter case, the second terminal 112 may proceed to a signing step only when the authentication is successful.

The producer checks the update information decrypted with an encryption key that may be symmetric to the requestor's public key and signs on the electronic contract (1633). The signature corresponds to verification of user authentication information and transaction approval. The second terminal 112 may encrypt (i) the update information or (ii) the update information and the signature with the requestor's public key $P1u_k$ (1633). The final electronic contract may include the requestor's hash key $H1_k$, the producer's hash key $H2_k$, the update information encrypted with the requestor's public key $P1u_k$, and the producer's signature key. The producer transmits the electronic contract including the signature and deletes target data.

The second terminal 112 generates electronic contract block data including the requestor's hash key $H1_k$, the producer's hash key $H2_k$, the update information encrypted with the requestor's public key $P1u_k$, and the producer's signature key (1641). The second terminal 112 delivers the generated electronic contract block data to the electronic contract blockchain 132 (1642). The electronic contract blockchain 132 registers the electronic contract block data (1643).

The electronic contract blockchain 132 may deliver the electronic contract to the first terminal 111 on the basis of the requestor's hash key $H1_k$ (1644). The first terminal 111 may decrypt the update information/signature included in the received electronic contract with its own encryption key and may check the details of the contract and the approval (1651).

Figure 21:
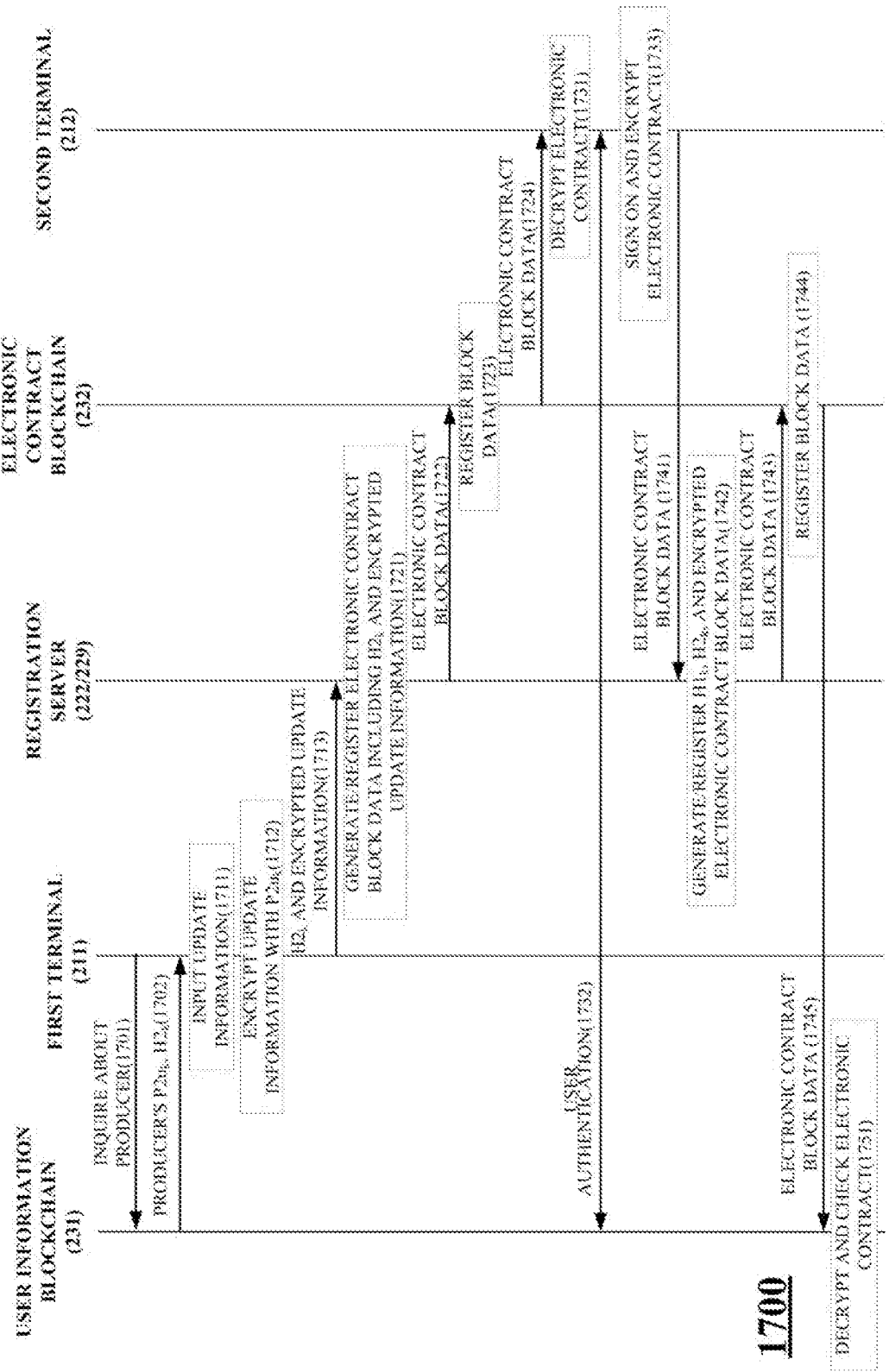
FIG. 21 illustrates another example process of updating a contract.

FIG. 21 illustrates another example process of updating a contract. FIG. 21 illustrates an example operation of the system 200 of FIG. 4 or 5. FIG. 21 shows an example process of changing and updating information regarding a contract between the requestor and the producer. The following description with reference to FIG. 21 focuses on the client and the producer, but the same process is applied to an update of a contract between the requestor and a third party. FIG. 21 illustrates an example in which a contract is updated to delete specific data when the contract ends or changes in condition. In other words, the example may be a process for deleting the specific data. Among user terminals in FIG. 21, a terminal 211 corresponding to the requestor is represented as a first terminal 211, and a terminal 213 corresponding to the producer is represented as a second terminal 212. It is assumed that the first terminal 211 and the second terminal 212 pre-registered their user information.

The first terminal 211 performs user authentication using the user information blockchain 231. When the authentication is successful, the first terminal 211 inquires of the user information blockchain 231 about the producer on the basis of information (user information) regarding the producer (1701). The first terminal 211 receives the producer's public key $P2u_k$ and hash key $H2_k$ from the user information blockchain 231 (1702).

The first terminal 211 inputs update information (1711). The update information includes information for changing the details of the contract. For example, the update information may include a change of a contract period, a change of requested details, a change of a contracting entity, a request to release a contract, contract end information, a request to delete bio-information data, a request to delete generated data, and the like. When the update information is a request to delete specific data, the update information may include an identifier of target data, producer information, requestor information, deletion conditions, etc. The first terminal 211 encrypts the update information with the public key $P2u_k$ (1712). The first terminal 211 transfers the hash key $H2_k$ and the encrypted update information to the electronic contract registration server 222 (1713).

The electronic contract registration server 222 generates electronic contract block data including the hash key $H2_k$ and the encrypted update information (1721). The electronic contract registration server 222 registers the generated electronic contract block data (1721).

The electronic contract registration server 222 delivers the generated electronic contract block data to the electronic contract blockchain 232 (1722). The electronic contract blockchain 232 registers the electronic contract block data including the encrypted update information and the hash key $H2_k$ (1723).

Subsequently, it may be checked whether the update information is forged or tampered. The user or another entity (a server in the system or an external server for forgery and tampering check) may check whether the update information is changed by comparing corresponding block data registered in the electronic contract registration server 222 to the reference block data stored in the electronic contract blockchain 232.

The electronic contract blockchain 232 transfers the electronic contract block data including the update information to the second terminal 212 on the basis of the hash key $H2_k$ (1724). The second terminal 212 decrypts the update information included in the block data with its own encryption key (1731). The second terminal 212 may perform user authentication through the user information blockchain 231 (1732). When the authentication is successful, the second terminal 212 may inquire of the user information blockchain 231 about the requestor's public key $P1u_k$ and hash key $H1_k$ and may receive the public key $P1u_k$ and the hash key $H1_k$ from the user information blockchain 231 (1732). Meanwhile, the update information may pre-include the requestor's public key $P1u_k$ and hash key $H1_k$. Even for the latter case, the second terminal 212 may proceed to a signing step only when the authentication is successful.

The producer checks the update information decrypted with an encryption key that may be symmetric to the requestor's public key and signs on the electronic contract (1733). The signature corresponds to verification of user authentication information and transaction approval for the producer. The second terminal 212 may generate a block including the update information, the signature, and the hash key. The second terminal 212 may encrypt (i) the update information or (ii) the update information and the signature with the requestor's public key $P1u_k$ (1733). The final electronic contract may include the requestor's hash key $H1_k$, the producer's hash key $H2_k$, the update information encrypted with the requestor's public key $P1u_k$, and the producer's signature key. The producer transmits the electronic contract including the signature and deletes target data.

The second terminal 212 transfers the generated electronic contract to the electronic contract registration server 222 (1741). The electronic contract registration server 222 generates electronic contract block data including the requestor's hash key $H1_k$, the producer's hash key $H2_k$, the update information encrypted with the requestor's public key $P1u_k$, and the producer's signature key (1742). The electronic contract registration server 222 registers the generated electronic contract block data (1742). The electronic contract registration server 222 delivers the generated electronic contract block data to the electronic contract blockchain 232 (1743). The electronic contract blockchain 232 registers the electronic contract block data (1744).

Subsequently, it may be checked whether the electronic contract is forged or tampered. The user or another entity (a server in the system or an external server for forgery and tampering check) may check whether the electronic contract is changed by comparing corresponding block data registered in the electronic contract registration server 222 to the reference block data stored in the electronic contract blockchain 232.

The electronic contract blockchain 232 may deliver the electronic contract to the first terminal 211 on the basis of the requestor's hash key $H1_k$ (1745). The first terminal 211 may decrypt the update information/signature included in the received electronic contract with its own encryption key and may check the details of the contract and the approval (1751).

Figure 22:
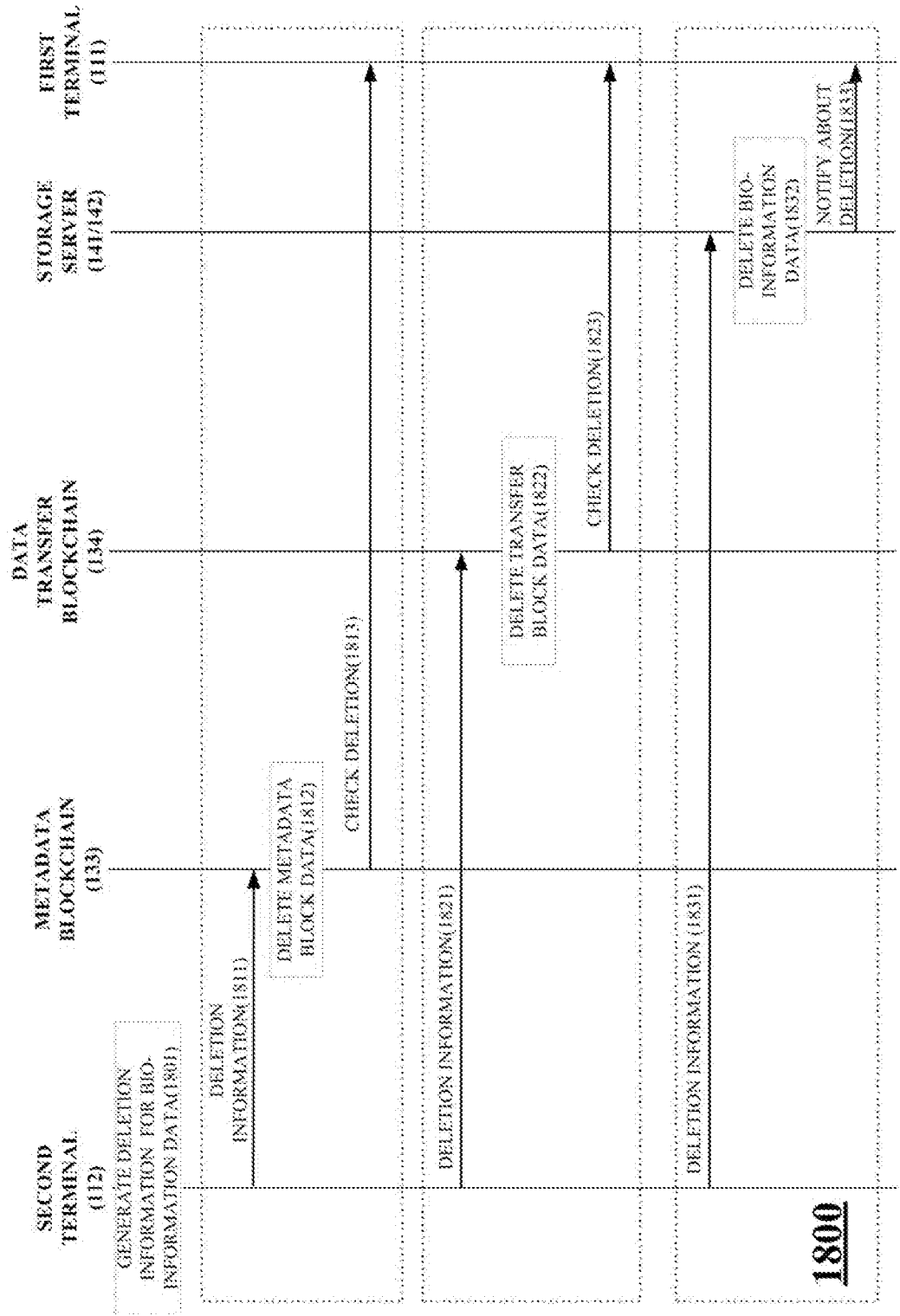
FIG. 22 illustrates an example process of deleting bio-information data and its associated data.

FIG. 22 is an example process of deleting bio-information data and its associated data. FIG. 22 is an example process of deleting specific data during a contract update operation. FIG. 22 is an example operation of the system 100 of FIG. 3. Among user terminals in FIG. 22, a terminal 111 corresponding to the requestor is represented as a first terminal 111, and a terminal 112 corresponding to the producer is represented as a second terminal 112. It is assumed that the first terminal 111 and the second terminal 112 pre-registered their user information.

FIG. 22 illustrates an example of a process for deleting metadata, storage block data, and transfer block data. Any or all of the specific data may be deleted according to the deletion information. Information generated by the second terminal 112 for the purpose of deletion may be referred to as deletion information.

When update information including a deletion request is received, the second terminal 112 generates deletion information for deleting the bio-information data and the associated data (1801). In this case, the deletion information may include (i) the requestor's hash key or the producer's hash key and (ii) additional information (a bio-information data identifier, a data generation time, etc.) for identifying specific metadata. The second terminal 112 delivers the deletion information to the metadata blockchain 133 (1811). The metadata blockchain 133 deletes the metadata block data held therein (1812).

The metadata blockchain 133 may notify the first terminal 111 of the deletion information on the basis of the requestor's hash key (1813).

When the update information is received, the second terminal 112 generates deletion information for deleting the bio-information data and the associated data (1801). In this case, the deletion information may include (i) the requestor's hash key or the producer's hash key and (ii) additional information (a bio-information data identifier, a data generation time, etc.) for identifying specific transfer information. The second terminal 112 delivers the deletion information to the data transfer blockchain 134 (1821). The data transfer blockchain 134 deletes the transfer block data held therein (1822). The data transfer blockchain 134 may notify the first terminal 111 of the deletion information on the basis of the requestor's hash key (1823).

When the deletion information is received, the second terminal 112 generates deletion information for deleting the bio-information data and the associated data (1801). In this case, the deletion information may include (i) the requestor's hash key or the producer's hash key and (ii) additional information (a bio-information data identifier, a data generation time, etc.) for identifying specific metadata. The second terminal 112 delivers the deletion information to a storage server 141 or 142 (1831). The storage server 141 or 142 may delete bio-information data held therein (1832). This means that the storage block data may be deleted from the data storage blockchain. The storage server 141 or 142 may notify the first terminal 111 of the deletion information (1833).

Figure 23:
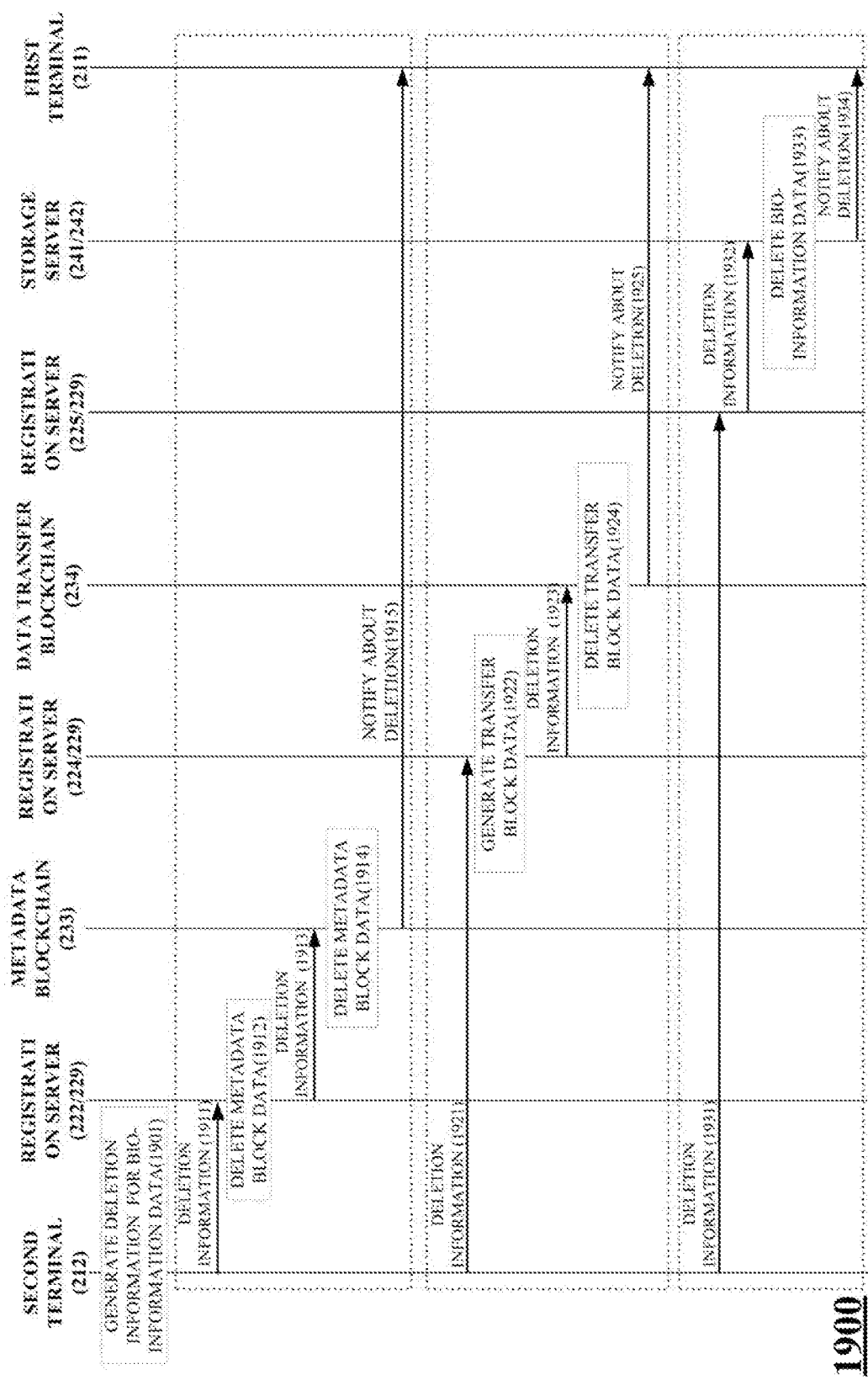
FIG. 23 illustrates another example process of deleting bio-information data and its associated data.

FIG. 23 illustrates another example process of deleting bio-information data and its associated data. FIG. 23 illustrates an example operation of the system 200 of FIG. 4 or 5. FIG. 23 is an example process of deleting specific data during a contract update operation. Among user terminals in FIG. 23, a terminal 211 corresponding to the requestor is represented as a first terminal 211, and a terminal 212 corresponding to the producer is represented as a second terminal 212. It is assumed that the first terminal 211 and the second terminal 212 pre-registered their user information. FIG. 23 shows a process of deleting metadata, storage block data, and transfer block data. Any or all of the specific data may be deleted according to the deletion information. Information generated by the second terminal 212 for the purpose of deletion is referred to as deletion information.

When the update information is received, the second terminal 212 generates deletion information for deleting the bio-information data and the associated data (1901). The second terminal 212 delivers the deletion information to a metadata registration server 223 (1911). In this case, the deletion information may include (i) the requestor's hash key or the producer's hash key and (ii) additional information (a genomic data identifier, a data generation time, etc.) for identifying specific metadata. The metadata registration server 223 deletes metadata block data held therein (1912). The metadata registration server 223 delivers the deletion information to the metadata blockchain 233 (1913). The metadata blockchain 233 deletes the metadata block data held therein (1914). The metadata blockchain 233 may notify the first terminal 211 of the deletion information on the basis of the requestor's hash key (1915).

When the deletion information is received, the second terminal 212 generates deletion information for deleting the bio-information data and the associated data (1901). The second terminal 212 delivers the deletion information to an information transfer registration server 224 (1921). In this case, the deletion information may include (i) the requestor's hash key or the producer's hash key and (ii) additional information (a genomic data identifier, a data generation time, etc.) for identifying specific transfer information. The information transfer registration server 224 deletes the transfer block data held therein (1922). The information transfer registration server 224 delivers the deletion information to the data transfer blockchain 234 (1923). The data transfer blockchain 234 deletes the transfer block data held therein (1924). The data transfer blockchain 234 may notify the first terminal 211 of the deletion information on the basis of the requestor's hash key (1925).

When the deletion information is received, the second terminal 212 generates deletion information for deleting the bio-information data and the associated data (1901). The second terminal 212 delivers the deletion information to a data storage registration server 225 (1931). In this case, the deletion information may include (i) the requestor's hash key or the producer's hash key and (ii) additional information (a genomic data identifier, a data generation time, etc.) for identifying specific metadata. The data storage registration server 225 delivers the deletion information to the storage server 241 or 242 (1932). The storage server 241 or 242 may delete the metadata block data held therein (1933). This means that the storage block data may be deleted from the data storage blockchain. The storage server 241 or 242 may notify the first terminal 211 of the deletion information (1934).

Also, the above-described bio-information data transfer method, bio-information data production request method, and contract changing method may be implemented as a program (or an application) including an algorithm executable on a computer. The program may be stored and provided in a non-transitory computer readable medium.

According to the above description, it is possible to provide a transfer system capable of preventing exposure of bio-information data and also preventing forgery/tampering of genomic data by using blockchain technology. According to the above description, it is possible to decrease network loads of large-scale bio-information data by separating user authentication from data transfer. According to the above description, it is possible to track forgery, tampering, and a usage history of bio-information data by managing information regarding a process of requesting generation of the bio-information data, transferring the bio-information data, and the like.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of providing bio-information data based on a plurality of blockchains, the method comprising:
    storing, by a user blockchain node, user block data received from a plurality of user terminals of a plurality of users and including user information, a shared key, and a hash key for each user of the plurality of users;
    storing, by an electronic contract blockchain node, contract block data received from a second user terminal of a second user and including contract information for a first user requesting the second user to generate bio-information data, the first user and the second user being included in the plurality of users;
    storing, by a data transfer blockchain node, transfer block data received from the second user terminal of the second user and including storage information for at least one storage server that stores the bio-information data;
    authenticating the first user based on the user blockchain node; and
    delivering, when the first user is authenticated, the transfer block data from the data transfer blockchain node to a first user terminal of the first user.

2. The method of claim 1, wherein the contract block data comprises contract information of the first user, a hash key of the first user, a hash key of the second user, and a signature of the second user.

3. The method of claim 2, wherein the storing the contract block data comprises:
    storing, by the electronic contract blockchain node, first contract information, wherein the first contract information is encrypted by the first user with a shared key of the second user from the user blockchain node; and
    storing, by the electronic contract blockchain node, second contract information including the signature and a re-encrypted first contract information, wherein the re-encrypted first contract information is encrypted by the second user with a shared key of the first user.

4. The method of claim 1, wherein the transfer block data includes a hash key of the first user and a hash key of the second user received from the user blockchain node and also includes the storage information encrypted with a shared key of the first user.

5. The method of claim 1, wherein the storage information includes at least one of an identifier of the storage server, a location where the bio-information data is stored in a storage medium, a verification key, a file size, or file partitioning information.

6. The method of claim 1, wherein the storage server includes a plurality of storage servers, and
    wherein the bio-information data is stored in a data storage blockchain in which the plurality of storage servers operate as nodes, in a block data form including information regarding a file in which a hash key of the first user, a hash key of the second user, and the bio-information data are stored.

7. The method of claim 1, further comprising enabling a metadata blockchain node to store metadata of the bio-information data.

8. The method of claim 1, further comprising:
    storing, by the electronic contract blockchain node, new contract block data including new contract information between the first user and a third user; and
    storing, the data transfer blockchain node, new transfer block data including new storage information encrypted with a hash key of the third user and a public key of the third user.

9. The method of claim 1, further comprising:
    storing, by the electronic contract blockchain node, new contract block data including new contract information between the first user and the second user,
    wherein the new contract information includes at least one of deletion of the contract block data, deletion of the transfer block data, and deletion of the bio-information data.

10. The method of claim 1, further comprising:
    storing, by the at least one storage server, at least one of block data from a block data group including the user block data, the contract block data, or the transfer block data; and
    transferring, by the at least one storage server, the stored block data to an entity to check whether the stored block data is forged.

11. A method of storing bio-information data based on a plurality of blockchains, the method comprising:
    storing, by a user blockchain node, user block data received from a plurality of user terminals of a plurality of users and including user information, a shared key, and a hash key for each user of the plurality of users;
    storing, by a storage server, bio-information data that is requested by a first user and generated by and received from a second user terminal of a second user, the first user and the second user being included in the plurality of users; and
    storing, by a data transfer blockchain node, transfer block data received from the second user terminal of the second user and including storage information of the storage server that stores the bio-information data,
    wherein the first user is authenticated based on the user blockchain node, and
    wherein, when the first user is authenticated, the transfer block data is delivered from the data transfer blockchain node to the first user.

12. The method of claim 11, wherein the transfer block data includes a hash key of the first user and a hash key of the second user received from the user blockchain node and also includes the storage information encrypted with a shared key of the first user.

13. The method of claim 11, wherein the storage information includes at least one of an identifier of the storage server, a location where the bio-information data is stored in a storage medium, a verification key, a file size, or file partitioning information.

14. The method of claim 11, wherein the storage server includes a plurality of servers, and the plurality of servers constitute a blockchain that stores the bio-information data.

15. A system for transferring bio-information data based on a plurality of blockchains, the system comprising:
    a user blockchain node configured to store user block data received from a plurality of user terminals of a plurality of users and including user information, a shared key, and a hash key for each user of the plurality of users;
    an electronic contract blockchain node configured to store contract block data received from a second user terminal of a second user and including contract information for a first user requesting the second user to generate bio-information data, the first user and the second user being included in the plurality of users;
    a storage server configured to store the bio-information data generated by and received from the second user; and a data transfer blockchain node configured to store transfer block data received from the second user terminal of the second user and including storage information for the storage server, wherein the first user is authenticated based on the user blockchain node, wherein, when the first user is authenticated, the transfer block data is delivered from the data transfer blockchain node to the first user, and wherein the user block data, the contract block data, and the transfer block data are generated by at least one of the first user or the second user.

16. The system of claim 15, wherein the contract block data comprises contract information of the first user, a hash key of the first user, a hash key of the second user, and a signature of the second user.

17. The system of claim 15, wherein the transfer block data includes a hash key of the first user and a hash key of the second user received from the user blockchain node and also includes the storage information encrypted with a shared key of the first user.

18. The system of claim 15, wherein the storage information includes at least one of an identifier of the storage server, a location where the bio-information data is stored in a storage medium, a verification key, a file size, or file partitioning information.

19. The system of claim 15, wherein the storage server includes a plurality of servers, and the plurality of servers constitute a blockchain that stores the bio-information data.

* * * * *